(12) United States Patent
Roeger et al.

(10) Patent No.: US 11,278,701 B2
(45) Date of Patent: Mar. 22, 2022

(54) APPARATUS INCLUDING MULTIPLE JOINED HYPOTUBES AND METHOD OF MAKING SAME

(71) Applicant: Lake Region Manufacturing, Inc., Chaska, MN (US)

(72) Inventors: Brent Roeger, Minneapolis, MN (US); Arne Rimmereide, Carver, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 799 days.

(21) Appl. No.: 15/729,847

(22) Filed: Oct. 11, 2017

(65) Prior Publication Data

US 2018/0104441 A1  Apr. 19, 2018

Related U.S. Application Data

(60) Provisional application No. 62/407,590, filed on Oct. 13, 2016, provisional application No. 62/407,568, filed on Oct. 13, 2016.

(51) Int. Cl.
*A61M 25/00* (2006.01)
*B23K 26/282* (2014.01)
(Continued)

(52) U.S. Cl.
CPC ......... *A61M 25/0009* (2013.01); *A61L 31/14* (2013.01); *A61M 25/0053* (2013.01);
(Continued)

(58) Field of Classification Search
CPC .......... A61B 2017/00477; A61L 31/14; A61M 25/0009; A61M 25/0053; A61M 25/0141;
(Continued)

(56) References Cited

U.S. PATENT DOCUMENTS 3,175,284 A * 3/1965 Cotovsky ............. B23K 20/129
                                                    228/114
4,001,543 A * 1/1977 Bove ................... B23K 26/282
                                                    219/121.63
(Continued)

FOREIGN PATENT DOCUMENTS

CN         102441222      5/2012
EP          1788926      11/2016
(Continued)

OTHER PUBLICATIONS

Extended European Search Report, Application No. 17196417.4, dated Apr. 4, 2018.
(Continued)

*Primary Examiner* — Tu B Hoang
*Assistant Examiner* — Vy T Nguyen
(74) *Attorney, Agent, or Firm* — Michael P. Horvath

(57) ABSTRACT

In various examples, an apparatus includes a first hypotube formed from a first material and a second hypotube formed from a second material different from the first material. A first joint is formed between the first hypotube and the second hypotube, the first joint including a combination of the first material and the second material. The apparatus includes a sidewall and a passageway extending through the apparatus. The sidewall is formed by the first sidewall of the first hypotube, the second sidewall of the second hypotube, and the first joint. The apparatus includes an outer diameter that is substantially consistent along a length of the apparatus and an inner diameter that is substantially consistent along a length of the apparatus. In other examples, a method of joining the first hypotube to the second hypotube is contemplated.

26 Claims, 6 Drawing Sheets

(51) Int. Cl.
*A61L 31/14* (2006.01)
*B23K 1/005* (2006.01)
*A61B 17/00* (2006.01)
*A61M 25/01* (2006.01)
*A61M 25/09* (2006.01)

(52) U.S. Cl.
CPC .......... *B23K 1/0056* (2013.01); *B23K 26/282* (2015.10); *A61B 2017/00477* (2013.01); *A61M 25/0141* (2013.01); *A61M 25/09* (2013.01)

(58) Field of Classification Search
CPC ... A61M 25/09; B23K 1/0056; B23K 26/282; B23K 26/323; B62J 1/00; B62J 1/08
USPC .......... 219/121.63, 121.74, 121.78; 405/170; 228/114, 125, 199, 2.3; 600/585, 486; 29/700, 855, 854, 825; 604/528, 264; 285/148.11, 329
See application file for complete search history.

(56) References Cited

U.S. PATENT DOCUMENTS

| | | | |
|---|---|---|---|
| 4,429,211 A * | 1/1984 | Carstens | ................ B23K 26/04 |
| | | | 219/121.63 |
| 4,935,029 A * | 6/1990 | Matsutani | ........ A61B 17/06066 |
| | | | 606/223 |
| 5,720,300 A | 2/1998 | Fagan et al. | |
| 6,575,958 B1 | 6/2003 | Happ et al. | |
| 6,712,843 B2 | 3/2004 | Elliott et al. | |
| 7,018,346 B2 | 3/2006 | Griffin et al. | |
| 7,182,735 B2 | 2/2007 | Shireman et al. | |
| 7,532,920 B1 | 5/2009 | Ainsworth et al. | |
| 7,645,242 B1 | 1/2010 | Jalisi et al. | |
| 7,655,039 B2 | 2/2010 | Brady et al. | |
| 7,758,520 B2 | 7/2010 | Griffin et al. | |
| 7,785,273 B2 | 8/2010 | Eskuri et al. | |
| 7,824,369 B2 | 11/2010 | Cangialosi et al. | |
| 8,092,395 B2 | 1/2012 | Lupton et al. | |
| 8,257,278 B2 | 9/2012 | Howland et al. | |
| 8,292,940 B2 | 10/2012 | Olson et al. | |
| 8,382,739 B2 | 2/2013 | Walak et al. | |
| 8,487,210 B2 | 7/2013 | Specht et al. | |
| 8,569,625 B2 | 10/2013 | Slininger et al. | |
| 8,574,219 B2 | 11/2013 | Nardone et al. | |
| 8,940,014 B2 | 1/2015 | Gamarra et al. | |
| 2005/0137501 A1 * | 6/2005 | Euteneuer | ......... A61M 25/0054 |
| | | | 600/585 |
| 2006/0006649 A1 | 1/2006 | Galdonik et al. | |
| 2006/0047223 A1 * | 3/2006 | Grandfield | .............. A61P 35/02 |
| | | | 600/585 |
| 2006/0264904 A1 | 11/2006 | Kerby et al. | |
| 2008/0086110 A1 | 4/2008 | Galdonik et al. | |
| 2009/0228094 A1 | 9/2009 | Yan et al. | |
| 2011/0015714 A1 | 1/2011 | Atkinson et al. | |
| 2013/0226033 A1 | 8/2013 | Eskuri et al. | |
| 2014/0200555 A1 | 7/2014 | Simpson et al. | |
| 2015/0094616 A1 | 4/2015 | Simpson et al. | |
| 2015/0359547 A1 | 12/2015 | Vale et al. | |
| 2016/0030644 A1 | 2/2016 | Pulugurtha | |
| 2017/0368586 A1 * | 12/2017 | Schenk | ................. B21C 37/121 |

FOREIGN PATENT DOCUMENTS

| | | |
|---|---|---|
| JP | 200465797 | 3/2004 |
| WO | 9850098 | 11/1998 |
| WO | 9917827 | 4/1999 |
| WO | 2007047039 | 4/2007 |
| WO | 2016090175 | 6/2016 |

OTHER PUBLICATIONS

"Substantive Examination Report", Application No. 17196417.4, dated Jun. 17, 2020.

* cited by examiner

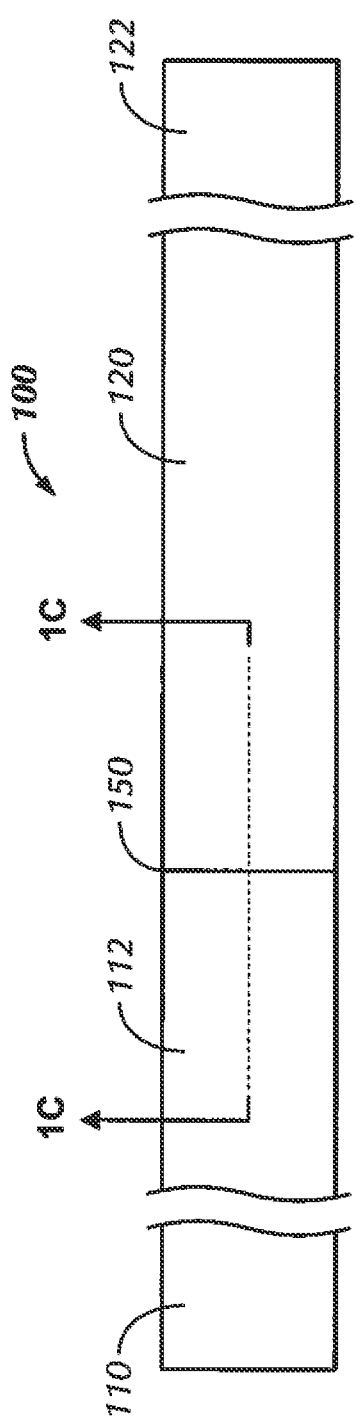
FIG. 1A
FIG. 1B
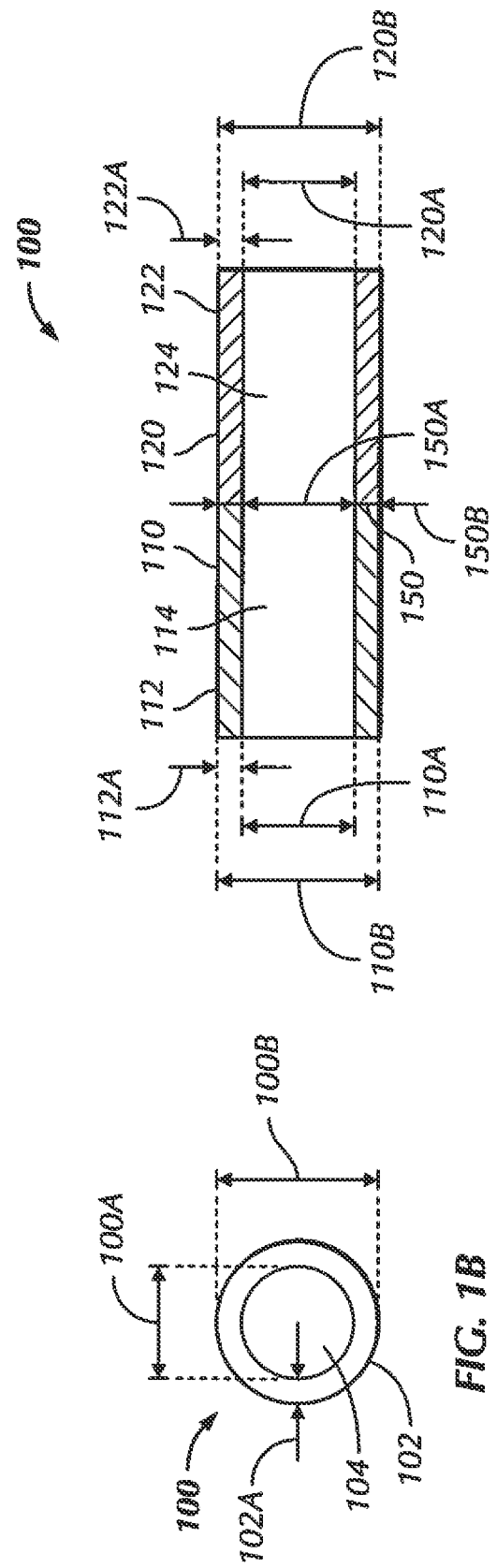
FIG. 1C

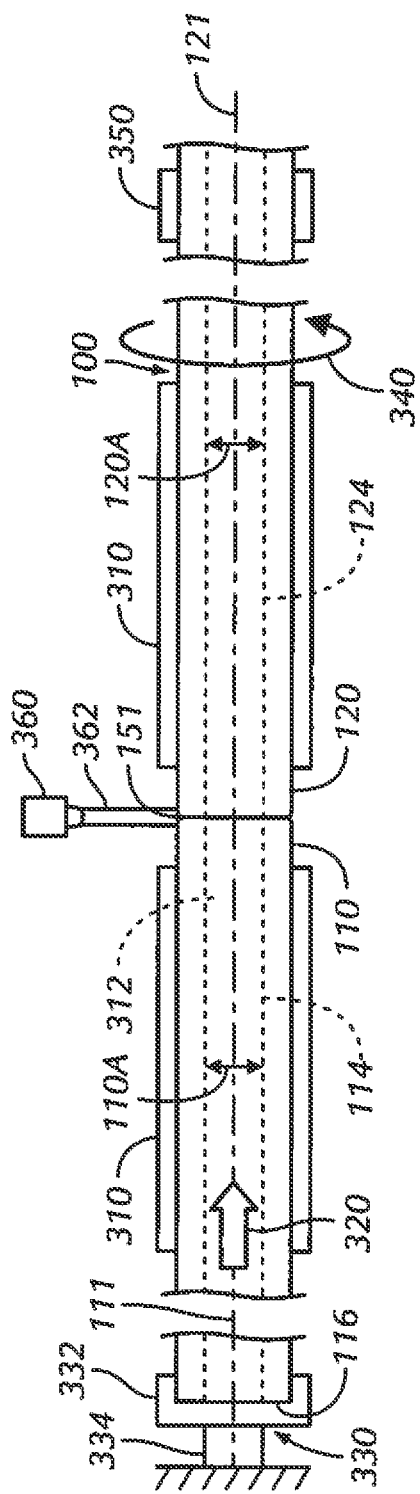
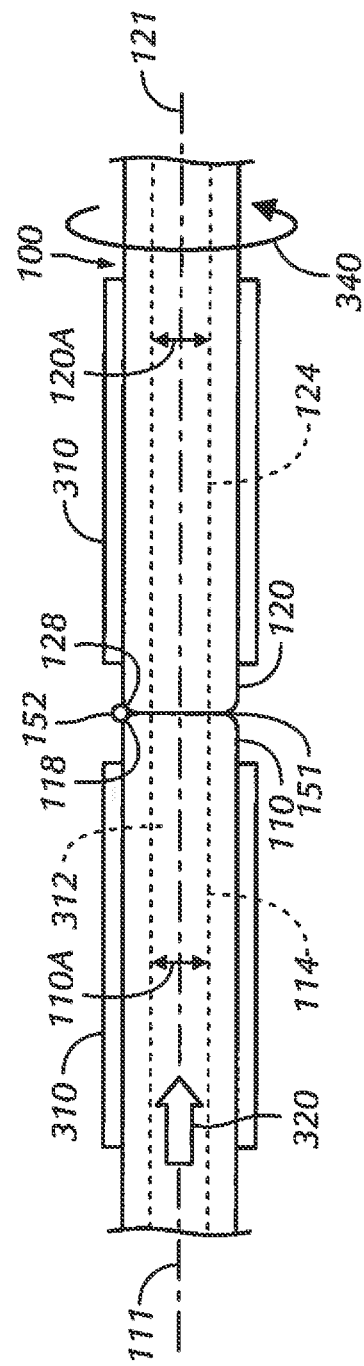
FIG. 3
FIG. 4

APPARATUS INCLUDING MULTIPLE JOINED HYPOTUBES AND METHOD OF MAKING SAME

CROSS REFERENCE TO RELATED APPLICATIONS

This application claims the benefit of priority to U.S. Provisional Application Ser. No. 62/407,568, filed on Oct. 13, 2016, entitled "A TWO JOINT DESIGN USING 3 HYPOTUBES; STIFF PROXIMAL SIDE HYPOTUBE, A STIFF INTERMEDIARY HYPOTUBE, AND A FLEXIBLE DISTAL TIP HYPOTUBE WITHOUT OR WITH THE USE OF MP35N, CO, NI, OR CU FILLER MATERIAL FOR THE WELDING JOINTS," and U.S. Provisional Application Ser. No. 62/407,590, filed on Oct. 13, 2016, entitled "HYPOTUBE ADDITIVE JOINT DESIGN USING MP35N FOR STIFFNESS AND NITINOL FOR FLEXIBILITY WITH USE OF MP35N, CO, NI, OR CU FILLER MATERIAL," each of which is incorporated by reference herein in its entirety.

BACKGROUND

The present invention relates to joining two or more hypotubes, and more specifically relates to a medical device including two or more joined hypotubes, the different hypotubes causing the medical device to have differing properties along its length.

A hypotube can be used as a passageway in a medical device to deliver sensor wire technologies, fiber optics, and other electronic devices to a location within a patient, oftentimes through tortuous blood vessel anatomy. It is often desirable that such medical devices include appropriate flexibility and performance against bending, pushability and torque transmission for transmitting an operational force from a proximal end portion to the distal side, and kink resistance (often called resistance against sharp bending). Conventional medical devices include a hypotube made of single material, such as either a stiff material like stainless steel (304 stainless steel, for instance) or a superelastic alloy like Nitinol (NiTi). A 304 stainless steel material has better stiffness and torquability than NiTi but relatively poor shape retention and kink resistance as compared to NiTi. On the other hand, NiTi does not provide as much stiffness as 304 stainless steel, and, as such, includes inferior torque transmission and/or control compared to 304 stainless steel.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to join tubes, such as hypotubes to be used within a medical device, in order to provide the medical device with a passageway therein while at the same time giving the medical device differing properties along its length. Joining hypotubes can be difficult due to the small size of the hypotubes. Moreover, maintaining a consistent passageway within the joined hypotubes can also be difficult due to the potential of material from the at least one joint entering the passageway during the joining process. The present inventors have recognized that the present subject matter can be used to join hypotubes of different materials to maintain a consistent passageway therein and provide the joined hypotubes with differing properties along the length of the joined hypotubes due to the different materials. The present inventors have further recognized that joined hypotubes of the present subject matter can be used within a medical device, such as, for instance, a guidewire. To better illustrate the apparatuses, systems, and methods described herein, a non-limiting list of examples is provided here:

Example 1 can include subject matter that can include an apparatus including a first hypotube formed from a first material and including a first sidewall and a first lumen defined within the first sidewall and extending through the first hypotube. The first hypotube includes a first inner diameter and a first outer diameter. A second hypotube is formed from a second material different from the first material and including a second sidewall and a second lumen defined within the second sidewall and extending through the second hypotube. The second hypotube includes a second inner diameter and a second outer diameter, wherein the second inner diameter is substantially similar to the first inner diameter and the second outer diameter is substantially similar to the first outer diameter. A first joint is between and joins the first hypotube and the second hypotube. The first joint includes a combination of the first material and the second material. The first joint includes a first joint inner diameter that is substantially similar to the first and second inner diameters, wherein the apparatus includes a sidewall and a passageway defined within the sidewall and extending through the apparatus. The sidewall is formed by the first sidewall, the second sidewall, and the first joint. The passageway is formed by the first lumen, the second lumen, and the first joint inner diameter. The apparatus includes an outer diameter that is substantially consistent along a length of the apparatus and an inner diameter that is substantially consistent along a length of the apparatus.

In Example 2, the subject matter of Example 1 is optionally configured such that the first material includes a kink-resistant material.

In Example 3, the subject matter of Example 1 or 2 is optionally configured such that the first material includes Nitinol.

In Example 4, the subject matter of any one of Examples 1-3 is optionally configured such that the second material includes a stiff material.

In Example 5, the subject matter of any one of Examples 1-4 is optionally configured such that the second material includes MP35N.

In Example 6, the subject matter of any one of Examples 1-5 is optionally configured such that the first joint includes a combination of the first material, the second material, and a filler.

In Example 7, the subject matter of any one of Examples 1-6 is optionally configured such that the first joint is formed by laser welding.

In Example 8, the subject matter of any one of Examples 1-7 is optionally configured such that the first joint includes a first joint outer diameter that is substantially similar to the first and second outer diameters.

In Example 9, the subject matter of any one of Examples 1-8 is optionally configured such that the first and second hypotubes are thin-walled hypotubes, wherein a wall thickness is between 0.00494 inches to 0.01082 inches for the first and second hypotubes having first and second outer diameters between 0.0236 inches to 0.0807 inches, respectively.

In Example 10, the subject matter of any one of Examples 1-9 is optionally configured such that the first and second hypotubes are extra-thin-walled hypotubes, wherein a wall thickness is between 0.00492 inches to 0.00832 inches for the first and second hypotubes having first and second outer diameters between 0.0236 inches to 0.0807 inches, respectively.

In Example 11, the subject matter of any one of Examples 1-10 optionally includes a third hypotube formed from a third material different from the second material and including a third sidewall and a third lumen defined within the third sidewall and extending through the third hypotube. The third hypotube including a third inner diameter and a third outer diameter, wherein the third inner diameter is substantially similar to the second inner diameter and the third outer diameter is substantially similar to the second outer diameter. A second joint is between and joins the second hypotube and the third hypotube. The second joint includes a combination of the second material and the third material. The second joint includes a second joint inner diameter that is substantially similar to the second and third inner diameters, wherein the sidewall of the apparatus is formed by the first sidewall, the second sidewall, the third sidewall, the first joint, and the second joint, and the passageway is formed by the first lumen, the second lumen, the third lumen, the first joint inner diameter, and the second joint inner diameter.

In Example 12, the subject matter of Example 11 is optionally configured such that the third material includes a stiff material.

In Example 13, the subject matter of Example 11 or 12 is optionally configured such that the third material includes stainless steel.

In Example 14, the subject matter of any one of Examples 11-13 is optionally configured such that the second joint is formed by laser welding.

In Example 15, the subject matter of any one of Examples 11-14 is optionally configured such that the first, second, and third hypotubes are thin-walled hypotubes.

In Example 16, the subject matter of any one of Examples 11-15 is optionally configured such that the first, second, and third hypotubes are extra-thin-walled hypotubes.

In Example 17, the subject matter of any one of Examples 11-16 is optionally configured such that the second joint includes a second joint outer diameter that is substantially similar to the second and third outer diameters.

Example 18 can include, or can optionally be combined with any one of Examples 1-17 to include subject matter that can include a method of joining two or more hypotubes together to form an apparatus. The method includes aligning a first hypotube with a second hypotube, wherein a first longitudinal axis of the first hypotube substantially coincides with a second longitudinal axis of the second hypotube. The first hypotube is formed from a first material and includes a first sidewall and a first lumen defined within the first sidewall and extending through the first hypotube. The first hypotube including a first inner diameter and a first outer diameter. The second hypotube is formed from a second material different from the first material and includes a second sidewall and a second lumen defined within the second sidewall and extending through the second hypotube. The second hypotube includes a second inner diameter and a second outer diameter, wherein the second inner diameter is substantially similar to the first inner diameter and the second outer diameter is substantially similar to the first outer diameter. A force is applied along the first longitudinal axis of the first hypotube to push the first hypotube toward and maintain contact against the second hypotube along a first intersection of the first hypotube and the second hypotube. The first hypotube is joined to the second hypotube at the first intersection of the first hypotube and the second hypotube to form a first joint. The first joint includes a combination of the first material and the second material. The first joint includes a first joint inner diameter that is substantially similar to the first and second inner diameters, wherein the apparatus includes a sidewall and a passageway defined within the sidewall and extending through the apparatus. The sidewall is formed by the first sidewall, the second sidewall, and the first joint. The passageway is formed by the first lumen, the second lumen, and the first joint inner diameter. The apparatus includes an outer diameter that is substantially consistent along a length of the apparatus and an inner diameter that is substantially consistent along a length of the apparatus.

In Example 19, the subject matter of Example 18 is optionally configured such that joining the first hypotube to the second hypotube includes laser welding the first hypotube to the second hypotube. The laser welding includes delivering one or more laser pulses at the first intersection of the first hypotube and the second hypotube.

In Example 20, the subject matter of Example 19 is optionally configured such that the laser welding includes imparting relative rotation between a laser emitter and the first and second hypotubes to laser weld around the first and second hypotubes along the first intersection.

In Example 21, the subject matter of any one of Examples 18-20 is optionally configured such that aligning the first hypotube with the second hypotube includes inserting an alignment wire within the first lumen and the second lumen to facilitate alignment of the first and second hypotubes.

In Example 22, the subject matter of any one of Examples 18-21 optionally includes adding a filler at the first intersection of the first and second hypotubes prior to joining the first and second hypotubes, wherein the first joint includes a combination of the first material, the second material, and the filler.

In Example 23, the subject matter of any one of Examples 18-22 is optionally configured such that the first material includes Nitinol.

In Example 24, the subject matter of any one of Examples 18-23 is optionally configured such that the second material includes MP35N.

In Example 25, the subject matter of any one of Examples 18-24 is optionally configured such that the first and second hypotubes are thin-walled hypotubes.

In Example 26, the subject matter of any one of Examples 18-25 is optionally configured such that the first and second hypotubes are extra-thin-walled hypotubes.

In Example 27, the subject matter of any one of Examples 18-26 is optionally configured such that the first joint includes a first joint outer diameter that is substantially similar to the first and second outer diameters.

In Example 28, the subject matter of any one of Examples 18-27 optionally includes aligning a third hypotube with the second hypotube, wherein a third longitudinal axis of the third hypotube substantially coincides with the second longitudinal axis of the second hypotube. The third hypotube being formed from a third material different from the second material and including a third sidewall and a third lumen defined within the third sidewall and extending through the third hypotube. The third hypotube includes a third inner diameter and a third outer diameter, wherein the third inner diameter is substantially similar to the second inner diameter and the third outer diameter is substantially similar to the second outer diameter. A force is applied along the second longitudinal axis of the second hypotube to push the second hypotube toward and maintain contact against the third hypotube along a second intersection of the second hypotube and the third hypotube. The third hypotube is joined to the second hypotube at the second intersection of the second hypotube and the third hypotube to form a second joint. The second joint includes a combination of the second material and the third material. The second joint includes a second joint inner diameter that is substantially similar to the second and third inner diameters, wherein the sidewall of the apparatus is formed by the first sidewall, the second sidewall, the third sidewall, the first joint, and the second joint, and the passageway is formed by the first lumen, the second lumen, the third lumen, the first joint inner diameter, and the second joint inner diameter.

In Example 29, the subject matter of Example 28 is optionally configured such that joining the third hypotube to the second hypotube includes laser welding the third hypotube to the second hypotube. The laser welding includes delivering one or more laser pulses at the second intersection of the third hypotube and the second hypotube.

In Example 30, the subject matter of Example 29 is optionally configured such that the laser welding includes imparting relative rotation between a laser emitter and the second and third hypotubes to laser weld around the second and third hypotubes along the second intersection.

In Example 31, the subject matter of any one of Examples 28-30 is optionally configured such that aligning the third hypotube with the second hypotube includes inserting an alignment wire within the second lumen and the third lumen to facilitate alignment of the second and third hypotubes.

In Example 32, the subject matter of any one of Examples 28-31 is optionally configured such that the third material includes stainless steel.

In Example 33, the subject matter of any one of Examples 28-32 is optionally configured such that the first, second, and third hypotubes are thin-walled hypotubes.

In Example 34, the subject matter of any one of Examples 28-33 is optionally configured such that the first, second, and third hypotubes are extra-thin-walled hypotubes.

In Example 35, the subject matter of any one of Examples 28-34 is optionally configured such that the second joint includes a second joint outer diameter that is substantially similar to the second and third outer diameters.

BRIEF DESCRIPTION OF THE DRAWINGS

FIG. 1A is a side view of two hypotubes joined in accordance with at least one example of the invention.

FIG. 1B is an end view of the joined hypotubes of FIG. 1A.

FIG. 1C is a cross-sectional view of the joined hypotubes taken along line 1C-1C of FIG. 1A.

FIG. 3 is a side view of a hypotube joining configuration in accordance with at least one example of the invention.

FIG. 4 is a side view of a hypotube joining configuration in accordance with at least one example of the invention.

DETAILED DESCRIPTION

Figure 2A:
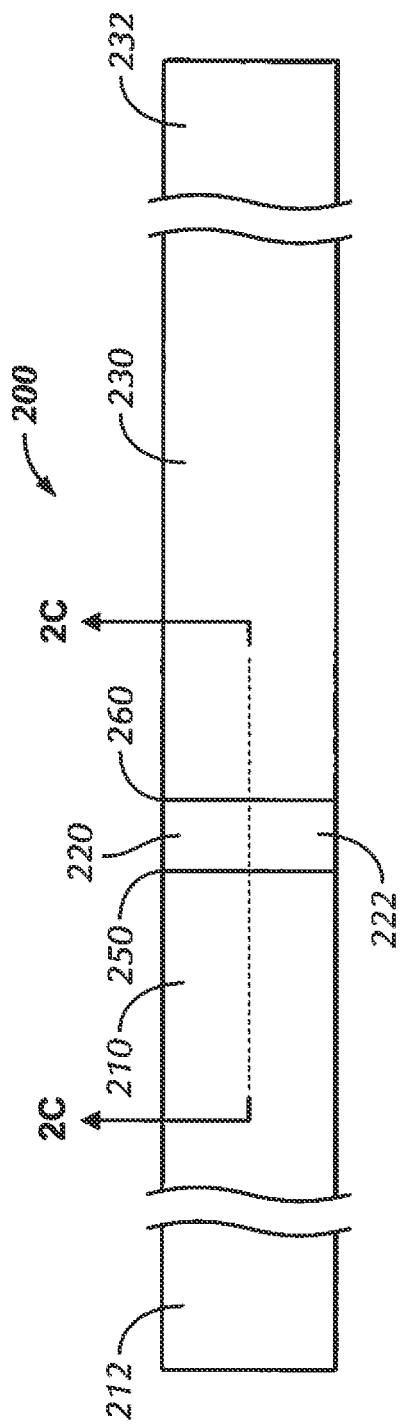
FIG. 2A is a side view of three hypotubes joined in accordance with at least one example of the invention.

In some examples, the present subject matter is directed to an apparatus having a joint that is made between at least two tubes of dissimilar materials, such as metals, each of the materials having different properties from one another, such that each of the tubes imparts differing characteristics to the apparatus. For instance, in some examples, an apparatus having a joint that is made between two tubes of dissimilar metals can provide adequate stiffness for support and torque transmission at a proximal end and kink-resistance at a distal end. In some examples, an apparatus is formed from two or more hypotubes joined together. In further examples, such an apparatus is included within a medical device. Stainless steel is commonly used in medical devices and can impart stiffness to the medical devices. Nitinol (NiTi) is also commonly used in medical devices and can impart kink-resistance to the medical devices. However, reliably joining Nitinol directly to stainless steel by fusion welding (such as by laser welding, for instance) is difficult, if not impossible, due to formation of brittle intermetallic alloys, which can compromise joint strength. However, the present inventors have recognized that formation of a joint with adequate strength and reliability can be accomplished using other materials, such as, for instance, MP35N (nickel-cobalt-based alloy), INCONEL® (nickel-chromium-based alloy), and MONEL® (nickel-copper-based alloy), which each contain ≤10% Fe and include relatively stiff material properties. Such materials can be used, in various examples, to form a good joint with NiTi without the formation of brittle intermetallic alloys and provide adequate stiffness for support and torque transmission in an apparatus. In some examples, an additional filler material, such as, but not limited to, MP35N, cobalt (Co), nickel (Ni), or copper (Cu) can further suppress additional brittle, intermetallic alloys (such as Ti-rich brittle, intermetallic alloys) from forming. The present patent application also relates to a method for joining tubes, such as hypotubes, for instance.

Referring now to FIGS. 1A-1C, in some examples, an apparatus 100 includes a first tube 110 joined to a second tube 120 at a first joint 150. In some examples, the first tube 110 is a first hypotube 110, and the second tube 120 is a second hypotube 120. As used herein, the term "hypotube" refers to a tube of any length that includes a relatively small outside diameter, such as an outside diameter between 0.005 inches and 0.25 inches. Although the examples herein largely refer to the first and second tubes 110, 120 as hypotubes, it is contemplated herein that the present subject matter can be used for tubes that are not considered hypotubes. Therefore, the description and figures herein should not be limited to only hypotubes.

In some examples, the apparatus 100 can be including within various devices, such as, but not limited to medical devices. For instance, in some examples, the apparatus 100 can be used as or within a guide wire, diagnostic wire, or other working wire to be used to navigate within a body of a patient. In other examples, the apparatus 100 can be used as or within other types of medical devices, such as catheters, sheaths, introducers, needles, infusion systems, laser ablation systems, or the like.

In some examples, the first hypotube 110 is formed from a first material. In some examples the first material is a metallic material. In some examples, the first material is a kink-resistant material to inhibit, if not eliminate, sharp bending of the first hypotube 110 and facilitate navigation within the body of the patient, such as through the vasculature of the patient, for instance. In some examples, the first material includes Nitinol (NiTi). The first hypotube 110, in some examples, includes a first sidewall 112 and a first lumen 114 defined within the first sidewall and extending through the first hypotube 110. The first sidewall 112, in some examples, includes a substantially consistent thickness 112A along the length of the first hypotube 110. In some examples, the first hypotube 110 includes a first inner diameter 110A and a first outer diameter 110B. In some examples, the first hypotube 110 is a thin-walled hypotube. As used herein, the phrase "thin-walled hypotube" refers to a hypotube having a relatively thin wall thickness. Although the thickness of a thin-walled hypotube wall varies as the outside diameter of the hypotube varies, generally increasing as the outside diameter of the hypotube increases, in the outside diameter range of 0.0236 inches to 0.0807 inches, the range of wall thickness is 0.00494 inches to 0.01082 inches for a thin-walled hypotube. (See ISO 9626.) In some examples, the first hypotube 110 is an extra-thin-walled hypotube. As used herein, the phrase "extra-thin-walled hypotube" refers to a hypotube having a very thin wall thickness. Although the thickness of an extra-thin-walled hypotube wall varies as the outside diameter of the hypotube varies, generally increasing as the outside diameter of the hypotube increases, in the outside diameter range of 0.0236 inches to 0.0807 inches, the maximum wall thickness to be considered an extra-thin-walled hypotube is in the range of 0.00492 inches to 0.00832 inches. (See ISO 9626.) When comparing a thin-walled hypotube of a particular outer diameter to an extra-thin-walled hypotube of the same outer diameter, the extra-thin-walled hypotube include smaller wall thickness than the thin-walled hypotube.

The second hypotube 120, in some examples, is formed from a second material different from the first material. In some examples the second material is a metallic material. In some examples, the second material is a relatively stiff material, such as, for instance, a material that allows for adequate stiffness for support and torque transmission for the apparatus 100. In some examples, the second material includes MP35N. In some examples, the second material includes INCONEL® and/or MONEL®. In some examples, the second hypotube 120 includes a second sidewall 122 and a second lumen 124 defined within the second sidewall 122 and extending through the second hypotube 120. The second sidewall 122, in some examples, includes a substantially consistent thickness 122A along the length of the second hypotube 120. In some examples, the second hypotube 120 includes a second inner diameter 120A and a second outer diameter 120B. In some examples, the second hypotube 120 is a thin-walled hypotube. In some examples, the second hypotube 120 is an extra-thin-walled hypotube. In some examples, the second hypotube 120 includes a second inner diameter 120A and a second outer diameter 120B. In some examples, the second inner diameter 120A is substantially similar to the first inner diameter 110A, and the second outer diameter 120B is substantially similar to the first outer diameter 110B.

In some examples, the first joint 150 is between the first hypotube 110 and the second hypotube 120, joining the first hypotube 110 and the second hypotube 120 together. The first joint 150, in some examples, includes a combination of the first material and the second material. In some examples, the first joint 150 is formed by laser welding. In some examples, a filler is included with the first joint 150, such that the first joint 150 includes a combination of the first material, the second material, and the filler. The filler, in various examples, can include one or more of MP35N, cobalt (Co), nickel (Ni), and/or copper (Cu). Regardless of whether a filler is used in the first joint 150, the first joint 150 securely and reliably joins the first hypotube 110 and second hypotube 120 to allow for the apparatus 100 to be used in various applications, such as medical applications, for instance, with confidence that the integrity of the first joint 150 will remain intact during use.

In some examples, the first joint 150 includes a first joint inner diameter 150A that is substantially similar to the first and second inner diameters 100A, 120A and a first joint outer diameter 150B that is substantially similar to the first and second outer diameters 110B, 120B. That is, the first hypotube 110 and the second hypotube 120 are joined together at the first joint 150 with little to no bump, ridge, or other bulge or expansion of material in from the first and second inner diameters 110A or out from the first and second outer diameters 110B.

The apparatus 100, in some examples, includes a sidewall 102 and a passageway 104 defined within the sidewall 102, the passageway 104 extending through the apparatus 100. In some examples, the sidewall 102 is formed by the first sidewall 112, the second sidewall 122, and the first joint 150. In further examples, the passageway 104 is formed by the first lumen 114, the second lumen 124, and the first joint inner diameter 150A. In some examples, the apparatus 100 includes an outer diameter 100B that is substantially consistent along a length of the apparatus 100 and an inner diameter 100A that is substantially consistent along a length of the apparatus 100. That is, in some examples, a thickness 102A of the sidewall 102 of the apparatus 100 is substantially equal along the length of the apparatus 100, regardless of whether the thickness 102A is measured at a point along the apparatus 100 that is formed by the first hypotube 110, the second hypotube 120, the first joint 150, or a combination thereof. In some examples, passing an object (such as, but not limited to a wire, a cable, a fiber, a stylet) or a fluid within or through the passageway 104 is facilitated by maintaining the inner diameter 100A of the apparatus 100 at a substantially consistent size along the length of the apparatus 100 and free from obstructions, particularly in the vicinity of the first joint 150. In like manner, in some examples, feeding of the apparatus 100 through or within a device or other object is facilitated by maintaining the outer diameter 100B of the apparatus 100 at a substantially consistent size along the length of the apparatus 100 and free from obstructions, particularly in the vicinity of the first joint 150.

Due to the first hypotube 110 being formed from the first material and the second hypotube 120 being formed from the second material, in some examples, the apparatus 100 includes varying characteristics along the length of the apparatus 100. For the example in which the first material includes Nitinol and the second material includes MP35N, the apparatus 100 includes a portion that is flexible and kink resistant and facilitates navigation through vasculature with the first hypotube 110 and a portion that is relatively stiff for support, torque transfer, pushability, and steering with the second hypotube 120. In some examples, a distal end of the apparatus 100 can include the first hypotube 110 (formed from Nitinol, in some examples), such that the distal end of the apparatus 100 is kink-resistant and flexible, and a proximal end of the apparatus 100 can include the second hypotube 120 (formed from MP35N, in some examples), such that the proximal end of the apparatus 100 is relatively stiff. In this way, the apparatus 100, in some examples, can be disposed within a medical device, such as a guidewire, for instance, and can be used to allow for flexibility and bending at the distal end for navigation of the apparatus 100 and pushability and torque transfer at the proximal end for advancing/withdrawing and steering of the apparatus 100. Although such a configuration can be used, in some examples, in medical devices, such as, for instance, guidewires, this is not to be considered limiting, in that the examples described can be used in a whole array of various devices, medical or otherwise. Moreover, in other examples, different materials can be used for one or both of the first and second hypotubes 110, 120 to achieve different characteristics of the apparatus 100. That is, in some examples, the materials chosen for the first and second materials of the first and second hypotubes 110, 120 can be tuned to achieve the proper characteristics for the apparatus 100 based upon the desired use of the apparatus 100.

Figure 2B:
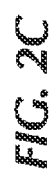
FIG. 2B is an end view of the joined hypotubes of FIG. 2A.
Figure 2C:
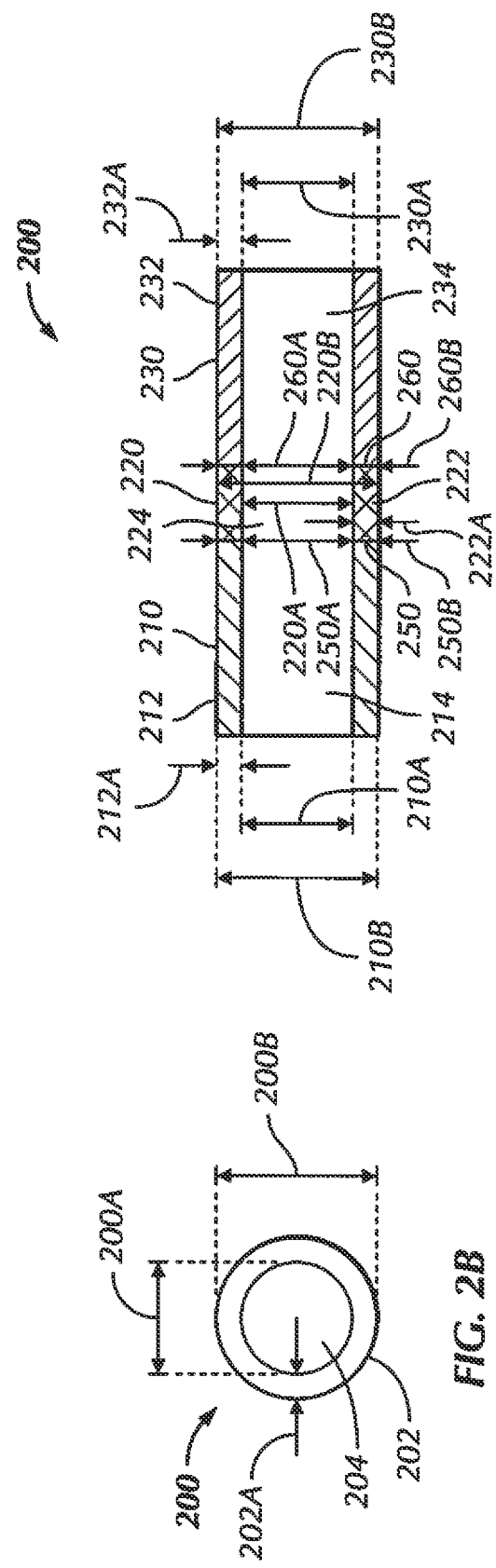
FIG. 2C is a cross-sectional view of the joined hypotubes taken along line 2C-2C of FIG. 2A.

Referring now to FIGS. 2A-2C, in some examples, an apparatus 200 includes a first tube 210 joined to a second tube 220 at a first joint 250 and a third tube 230 joined to the second tube 220 at a second joint 260. In some examples, the first tube 210 is a first hypotube 210, the second tube 220 is a second hypotube 220, and the third tube 230 is a third hypotube 230. Although the examples herein largely refer to the first, second, and third tubes 210, 220, 230 as hypotubes, it is contemplated herein that the present subject matter can be used for tubes that are not considered hypotubes. Therefore, the description and figures herein should not be limited to only hypotubes.

In some examples, the apparatus 200 can be included within various devices, such as, but not limited to medical devices. For instance, in some examples, the apparatus 200 can be used within a guide wire, diagnostic wire, or other working wire to be used to navigate within a body of a patient. In other examples, the apparatus 200 can be used within other types of medical devices, such as catheters, sheaths, introducers, needles, infusion systems, laser ablation systems, or the like.

In some examples, the first hypotube 210 is formed from a first material. In some examples the first material is a metallic material. In some examples, the first material is a kink-resistant material to inhibit, if not eliminate, sharp bending of the first hypotube 210 and facilitate navigation within the body of the patient, such as through the vasculature of the patient, for instance. In some examples, the first material includes Nitinol (NiTi). The first hypotube 210, in some examples, includes a first sidewall 212 and a first lumen 214 defined within the first sidewall and extending through the first hypotube 210. The first sidewall 212, in some examples, includes a substantially consistent thickness 212A along the length of the first hypotube 210. In some examples, the first hypotube 210 includes a first inner diameter 210A and a first outer diameter 210B. In some examples, the first hypotube 210 is a thin-walled hypotube. In some examples, the first hypotube 210 is an extra-thin-walled hypotube.

The second hypotube 220, in some examples, is formed from a second material different from the first material. In some examples the second material is a metallic material. In some examples, the second material is a relatively stiff material, such as, for instance, a material that allows for adequate stiffness for support and torque transmission for the apparatus 200. In some examples, the second material includes MP35N. In some examples, the second material includes INCONEL® and/or MONEL®. In some examples, the second hypotube 220 includes a second sidewall 222 and a second lumen 224 defined within the second sidewall 222 and extending through the second hypotube 220. The second sidewall 222, in some examples, includes a substantially consistent thickness 222A along the length of the second hypotube 220. In some examples, the second hypotube 220 includes a second inner diameter 220A and a second outer diameter 220B. In some examples, the second hypotube 220 is a thin-walled hypotube. In some examples, the second hypotube 220 is an extra-thin-walled hypotube. In some examples, the second hypotube 220 includes a second inner diameter 220A and a second outer diameter 220B. In some examples, the second inner diameter 220A is substantially similar to the first inner diameter 210A, and the second outer diameter 220B is substantially similar to the first outer diameter 210B.

In some examples, the first joint 250 is between the first hypotube 210 and the second hypotube 220, joining the first hypotube 210 and the second hypotube 220 together. The first joint 250, in some examples, includes a combination of the first material and the second material. In some examples, the first joint 250 is formed by laser welding. In some examples, a filler is included with the first joint 250, such that the first joint 250 includes a combination of the first material, the second material, and the filler. The filler, in various examples, can include one or more of MP35N, cobalt (Co), nickel (Ni), and/or copper (Cu). Regardless of whether a filler is used in the first joint 250, the first joint 250 securely and reliably joins the first hypotube 210 and second hypotube 220 to allow for the apparatus 200 to be used in various applications, such as medical applications, for instance, with confidence that the integrity of the first joint 250 will remain intact during use.

In some examples, the first joint 250 includes a first joint inner diameter 250A that is substantially similar to the first and second inner diameters 210A, 220A and a first joint outer diameter 250B that is substantially similar to the first and second outer diameters 210B, 220B. That is, the first hypotube 210 and the second hypotube 220 are joined together at the first joint 250 with little to no bump, ridge, or other bulge or expansion of material in from the first and second inner diameters 210A, 220A or out from the first and second outer diameters 210B, 220B.

The third hypotube 230, in some examples, is formed from a third material different from the second material. In some examples the third material is a metallic material. In some examples, the third material is a relatively stiff material, such as, for instance, a material that allows for adequate stiffness for support and torque transmission for the apparatus 200. In some examples, the third material includes stainless steel. In further examples, the third material includes 304 stainless steel. In other examples, the third material can include 302 stainless steel, 316 stainless steel, 440 stainless steel, 715 stainless steel, or the like. In some examples, the third hypotube 230 includes a third sidewall 232 and a third lumen 234 defined within the third sidewall 232 and extending through the third hypotube 230. The third sidewall 232, in some examples, includes a substantially consistent thickness 232A along the length of the third hypotube 230. In some examples, the third hypotube 230 includes a third inner diameter 230A and a third outer diameter 230B. In some examples, the third hypotube 230 is a thin-walled hypotube. In some examples, the third hypotube 230 is an extra-thin-walled hypotube. In some examples, the third hypotube 230 includes a third inner diameter 230A and a third outer diameter 230B. In some examples, the third inner diameter 230A is substantially similar to the second inner diameter 220A, and the third outer diameter 230B is substantially similar to the second outer diameter 220B.

In some examples, the second joint 260 is between the second hypotube 220 and the third hypotube 230, joining the second hypotube 220 and the third hypotube 230 together. The second joint 260, in some examples, includes a combination of the second material and the third material. In some examples, the second joint 260 is formed by laser welding. The second joint 260 securely and reliably joins the second hypotube 220 and third hypotube 230 to allow for the apparatus 200 to be used in various applications, such as medical applications, for instance, with confidence that the integrity of the second joint 260 will remain intact during use.

In some examples, the second joint 260 includes a second joint inner diameter 260A that is substantially similar to the second and third inner diameters 220A, 230A and a second joint outer diameter 260B that is substantially similar to the second and third outer diameters 220B, 230B. That is, the second hypotube 220 and the third hypotube 230 are joined together at the second joint 260 with little to no bump, ridge, or other bulge or expansion of material in from the second and third inner diameters 220A, 230A or out from the second and third outer diameters 220B, 230B.

The apparatus 200, in some examples, includes a sidewall 202 and a passageway 204 defined within the sidewall 202, the passageway 204 extending through the apparatus 200. In some examples, the sidewall 202 is formed by the first sidewall 212, the second sidewall 222, the third sidewall 232, the first joint 250, and the second joint 260. In further examples, the passageway 204 is formed by the first lumen 214, the second lumen 224, the third lumen 234, the first joint inner diameter 250A, and the second joint inner diameter 260A. In some examples, the apparatus 200 includes an outer diameter 200B that is substantially consistent along a length of the apparatus 200 and an inner diameter 200A that is substantially consistent along a length of the apparatus 200. That is, in some examples, a thickness 202A of the sidewall 202 of the apparatus 200 is substantially equal along the length of the apparatus 200, regardless of whether the thickness 202A is measured at a point along the apparatus 200 that is formed by the first hypotube 210, the second hypotube 220, the third hypotube 230, the first joint 250, the second joint 260, or a combination thereof. In some examples, passing an object (such as, but not limited to a wire, a cable, a fiber, a stylet) or a fluid within or through the passageway 204 is facilitated by maintaining the inner diameter 200A of the apparatus 200 at a substantially consistent size along the length of the apparatus 200 and free from obstructions, particularly in the vicinity of the first joint 250 and/or the second joint 260. In like manner, in some examples, feeding of the apparatus 200 through or within a device or other object is facilitated by maintaining the outer diameter 200B of the apparatus 200 at a substantially consistent size along the length of the apparatus 200 and free from obstructions, particularly in the vicinity of the first joint 250 and/or the second joint 260.

Due to the first hypotube 210 being formed from the first material, the second hypotube 220 being formed from the second material, and the third hypotube 230 being formed from the third material, in some examples, the apparatus 200 includes varying characteristics along the length of the apparatus 200. For the example in which the first material includes Nitinol, the second material includes MP35N, and the third material includes stainless steel, the apparatus 200 includes a portion that is flexible and kink resistant and facilitates navigation through vasculature with the first hypotube 210 and a portion that is relatively stiff for support, torque transfer, pushability, and steering with the second hypotube 220 and/or the third hypotube 230. In some examples, a distal end of the apparatus 200 can include the first hypotube 210 (formed from Nitinol, in some examples), such that the distal end of the apparatus 200 is kink-resistant and flexible, and a proximal end of the apparatus 200 can include the second and third hypotubes 220, 230 (formed from MP35N and stainless steel, respectively, in some examples), such that the proximal end of the apparatus 200 is relatively stiff. In this way, the apparatus 200, in some examples, can be disposed within a medical device, such as a guidewire, for instance, and can be used to allow for flexibility and bending at the distal end for navigation of the apparatus 200 and pushability and torque transfer at the proximal end for advancing/withdrawing and steering of the apparatus 200. Although such a configuration can be used, in some examples, in medical devices, such as, for instance, guidewires, this is not to be considered limiting, in that the examples described can be used in a whole array of various devices, medical or otherwise. Moreover, in other examples, different materials can be used for one or more of the first, second, and third hypotubes 210, 220, 230 to achieve different characteristics of the apparatus 200. That is, in some examples, the materials chosen for the first, second, and third materials of the first, second, and third hypotubes 210, 220, 230 can be tuned to achieve the proper characteristics for the apparatus 200 based upon the desired use of the apparatus 200. Additionally, although the apparatus 200 is described as including three hypotubes 210, 220, 230 joined together, it is contemplated in some examples that the apparatus includes more than three hypotubes joined together. In some examples, the number of hypotubes joined together is dependent upon the properties and characteristics desired for the apparatus and the location or locations along the apparatus that those properties and characteristics are desired. Although the apparatus 200 is shown in FIG. 2A as having a relatively short second hypotube 220 in comparison with the first and third hypotubes 210, 230, it is noted that the first, second, and third hypotubes 210, 220, 230 can have various lengths depending upon what characteristics are desired at which points along the apparatus 200.

Referring now to FIGS. 3-6, a method of joining the two or more hypotubes 110, 120, 210, 220, 230 together to form the apparatus 100, 200 is shown. Referring first to FIGS. 3 and 4, in some examples, the method is described to join the first and second hypotubes 110, 120 to form the apparatus 100, as described above and shown in FIGS. 1A-1C. In some examples, the first hypotube 110 is aligned with the second hypotube 120, such that a first longitudinal axis 111 of the first hypotube 110 substantially coincides with a second longitudinal axis 121 of the second hypotube 120. In some examples, the first and second hypotubes 110, 120 are loaded into one or more alignment members 310. In the examples shown in FIGS. 3 and 4, the one or more alignment members 310 include two containment hypotubes 310, the containment hypotubes 310 being sized such that the first and second hypotubes 110, 120 can fit and freely rotate and slide within the containment hypotubes 310. In this way, the containment tubes 310, in some examples, can be kept stationary and the first and second hypotubes 110, 120 can be rotated, translated, or otherwise moved with respect to the containment tubes 310, if desired, during the joining of the first and second hypotubes 110, 120. Although two containment hypotubes 310 are shown, it is contemplated that a single containment hypotube is used with a cutout, window, or other opening in the containment hypotube to allow access to the abutting first and second hypotubes 110, 120 for joining of the first and second hypotubes 110, 120. In other examples, other types of alignment devices are contemplated, such as, but not limited to one or more channels within one or more plates, blocks, angle irons, partial tubes, or other members.

In some examples, a force 320 is applied along the first longitudinal axis 111 of the first hypotube 110 to push the first hypotube 110 toward and maintain contact against the second hypotube 120 along a first intersection 151 of the first hypotube 110 and the second hypotube 120. In some examples, the force 320 can be applied to the first hypotube 110 by a pushing device 330. In some examples, the pushing device 330 includes a pushing surface 332 that interfaces with the first hypotube 110. In some examples, the pushing surface 332 abuts a first end 116 of the first hypotube 110. In other examples, the pushing device 330 includes other attachment devices for attaching to the first hypotube 110, including, but not limited to a clamp, a chuck, or the like. The pushing device 330, in some examples, includes a pushing member 334 to generate the force 320 to be applied to the first hypotube 110. In some examples, the pushing member 334 includes a spring to generate the force 320. In other examples, the pushing member 334 includes a piston to generate the force 320. In further examples, the pushing member 334 includes a pneumatic or hydraulic piston to generate the force 320.

In some examples, an alignment wire 312 can be inserted or otherwise placed within the first and second lumens 114, 124 to aid or facilitate in the alignment of the first and second hypotubes 110, 120. In some examples, the alignment wire 312 is sized to be slightly smaller in diameter than the inner diameters 110A, 120A of the first and second hypotubes 110, 120 in order to fit within and properly align the first and second lumens 114, 124 of the first and second hypotubes 110, 120, but also allow for relatively easy insertion into and withdrawal from the first and second lumens 114, 124. In other examples, no alignment wire 312 is used to align the first and second hypotubes 110, 120, with the containment tubes 310 or other alignment member or members 310 providing for alignment of the first and second hypotubes 110, 120.

In some examples, the first hypotube 110 is joined to the second hypotube 120 at the first intersection 151 of the first hypotube 110 and the second hypotube 120 to form the first joint 150 (FIGS. 1A-1C). Various techniques can be used to join the first and second hypotubes 110, 120, including, but not limited to, laser welding, ultra-sonic welding, plasma welding, friction welding, soldering, and/or other processes and/or one or more combinations thereof. In some examples, the first hypotube 110 is joined to the second hypotube 120 by laser welding the first hypotube 110 to the second hypotube 120. In some examples, the laser welding includes a laser emitter or head 360 to deliver one or more laser pulses 362 at the first intersection 151 of the first hypotube 110 and the second hypotube 120. In some examples, the laser emitter or head 360 can include a laser generator, one or more delivery optics, one or more focusing optics, or a combination thereof. In some examples, if the alignment wire 312 is used to facilitate alignment of the first and second hypotubes 110, 120, once at least one laser pulse 362 is delivered, the alignment wire 312 can be removed. The at least one laser pulse 362 tacks the first and second hypotubes 110, 120 together, thereby inhibiting relative movement between the first and second hypotubes 110, 120 so that the alignment wire 312 can be removed from within the first and second hypotubes 110, 120. In some examples, additional laser pulses 362 can be delivered to the first intersection 151 to further join the first and second hypotubes 110, 120.

In some examples, relative rotation is imparted between the laser emitter or head 360 and the first and second hypotubes 110, 120 to laser weld around the first and second hypotubes 110, 120 along the first intersection 151. In some examples, the first and second hypotubes 110, 120 are rotated with respect to the laser emitter or head 360. For instance, in some examples, a clamping device 350 is attached to the second hypotube 120, the clamping device 350 being rotatable to impart rotation 340 to the second hypotube 120, and, in turn, the first hypotube 110 once the first hypotube 110 is at least tacked to the second hypotube 120. In some examples, the first and second hypotubes 110, 120 are rotated to deliver laser pulses 362 along the entire circumference of the first intersection 151 of the first and second hypotubes 110, 120 to create the first joint 150. In other examples, the first and second hypotubes 110, 120 are kept stationary and the laser emitter or head 360 is rotated with respect to the first and second hypotubes 110, 120 in order to laser weld the entire circumference of the first intersection 151 to create the first joint 150.

In some examples, one or more pulse profiles of the one or more laser pulses 362 are shaped, tuned, or otherwise configured to deliver energy to the first and second hypotubes 110, 120 at the first intersection 151 to sufficiently fuse the first and second hypotubes 110, 120 while at the same time inhibiting, if not preventing, the first and/or second materials of the first and second hypotubes 110, 120 from migrating into the first lumen 114 and/or the second lumen 124 to maintain the passageway 104 of the apparatus 100 (FIGS. 1A-1C) free from obstructions. In some examples, the one or more laser pulses 362 are tuned or configured to deliver energy to the first and second hypotubes 110, 120 at the first intersection 151 to sufficiently fuse the first and second hypotubes 110, 120 while at the same time inhibiting, if not preventing, the first and/or second materials of the first and second hypotubes 110, 120 from extending outwardly from the first sidewall 112 and/or the second sidewall 122 to maintain the sidewall 102 of the apparatus 100 (FIGS. 1A-1C) free from obstructions.

In some examples, the first intersection 151 is disposed between the containment hypotubes 310 to allow access by the laser emitter or head 360 and the one or more laser pulses 362 to the first intersection 151 in order to form the first joint 150. In other examples in which other alignment devices are contemplated, such as a single containment hypotube with a cutout, window, or other opening; one or more channels within one or more plates, blocks, angle irons, partial tubes, or other members; to name a few, the first intersection 151 is located to allow access to the first intersection 151 by the laser emitter or head 360 and the one or more laser pulses 362.

In some examples, as shown in FIG. 3, the first joint 150 is formed from the first material of the first hypotube 110 and the second material of the second hypotube 120 without the use of a filler. In other examples, as shown in FIG. 4, a filler 152 is used to make the first joint 150, such that the first joint 150 is formed from the first material of the first hypotube 110, the second material of the second hypotube 120, and the filler 152. In this way, in some examples, the filler 152 is added at the first intersection 151 of the first and second hypotubes 110, 120 prior to joining the first and second hypotubes 110, 120. Once the filler 152 is present at the intersection, the one or more laser pulses 362 can be applied to the first intersection 151 in order to fuse the first material, the second material, and the filler 152, such that the first joint 150 includes a combination of the first material, the second material, and the filler 152. The filler 152, in various examples, can include one or more of MP35N, cobalt (Co), nickel (Ni), and/or copper (Cu). The filler 152, in various examples, can be introduced to the first intersection 151 in various ways, such as, but not limited to, adding the filler 152 in the form of a wire, a powder, or a ball. In some examples, the filler 152 is introduced with the rotation 340 of the first and second hypotubes 110, 120. In other examples, if the first and second hypotubes 110, 120 are kept stationary, the filler 152 can be rotated around the first and second hypotubes 110, 120 along with the laser emitter or head 360 in order to introduce the filler 152 prior to laser welding. In some examples, the first intersection 151 is disposed between the containment hypotubes 310 to allow access to the first intersection 151 to add the filler 152 prior to laser welding. In other examples in which other alignment devices are contemplated, such as a single containment hypotube with a cutout, window, or other opening; one or more channels within one or more plates, blocks, angle irons, partial tubes, or other members; to name a few, the first intersection 151 is located to allow access to the first intersection 151 in order to add the filler 152 to the first intersection 151 prior to laser welding.

In some examples, at least one of the first and second hypotubes 110, 120 can include a reduced edge 118, 128 along the first intersection 151. For instance, in some examples, the first hypotube 110 includes a first reduced edge 118, and the second hypotube 120 includes a second reduced edge 128. In various examples, the first and second hypotubes 110, 120 can be ground down, cut, filed, or otherwise removed to form the first and second reduced edges 118, 128. In other examples, the first and second hypotubes 110, 120 can be formed to include the first and second reduced edges 118, 128. The first and second reduced edges 118, 120, in some examples, can include a rounded shape, a tapered shape, or the like. With one or both of the first and second hypotubes 110, 120 including the reduced edge 118, 128, the filler 152 can be added to the first intersection 151 and the first intersection 151 can be welded to form the first joint 150 without the first joint 150 expanding beyond the first and second inner diameters 110A, 120A of the first and second hypotubes 110, 120 or the first and second outer diameters 110B, 120B of the first and second hypotubes 110, 120, thereby maintaining substantially consistent dimensions of the passageway 104 and the sidewall 102 of the apparatus 100. That is, with one or both of the first and second reduced edges 118, 128, the removal of the first and/or second materials of the first and/or second hypotubes 110, 120 makes room for the addition of the filler 152 without increasing the overall volume of the materials making up the first joint 150 to allow for the dimensions of the first joint 150 to remain substantially consistent with the dimensions of the first hypotube 110 and the second hypotube 120, thereby allowing for the passageway 104 and the sidewall 102 of the apparatus 100 to maintain substantially consistent dimensions along the length of the apparatus 100. In some examples, both of the first and second hypotubes 110, 120 include reduced edges 118, 128. In other examples, only the first hypotube 110 includes the first reduced edge 118, with the second hypotube 120 including a normal, unreduced edge. In still other examples, only the second hypotube 120 includes the second reduced edge 128, with the first hypotube 110 including a normal, unreduced edge.

In some examples, once the first joint 150 is completed, the first and second hypotubes 110, 120 are joined together to form the apparatus 100, which can be removed from within the containment tubes 310 or other alignment device (s). The apparatus 100, in some examples, forms a continuous hypotube with differing characteristics along the length of the apparatus 100 due to the different materials used for the first and second hypotubes 110, 120, which make up the apparatus 100. For instance, in the example in which the first hypotube 110 is formed from Nitinol and the second hypotube 120 is formed from MP35N, the apparatus 100 includes flexibility, shape retention, and kink-resistance in the portion of the apparatus 100 formed by the first hypotube 110 and stiffness and torquability in the portion of the apparatus 100 formed by the second hypotube 120.

Figure 5:
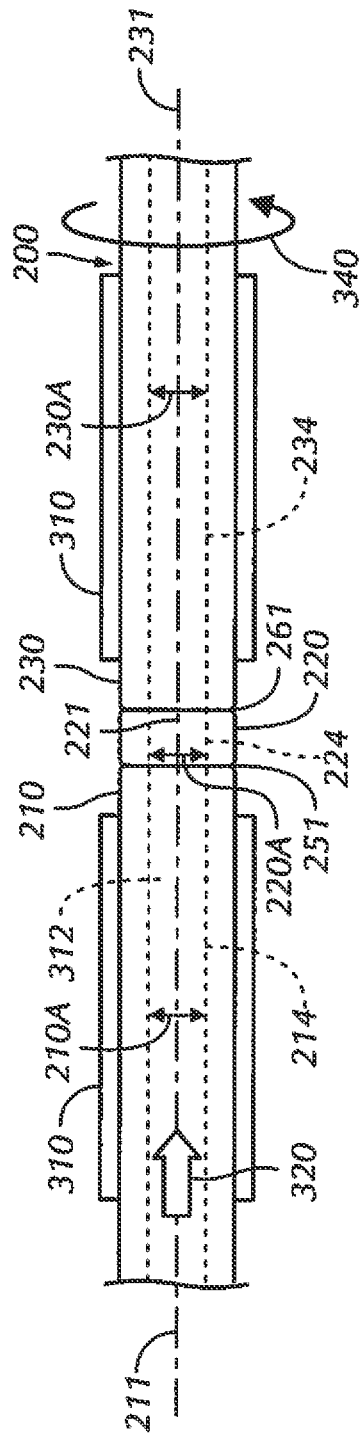
FIG. 5 is a side view of a hypotube joining configuration in accordance with at least one example of the invention.
Figure 6:
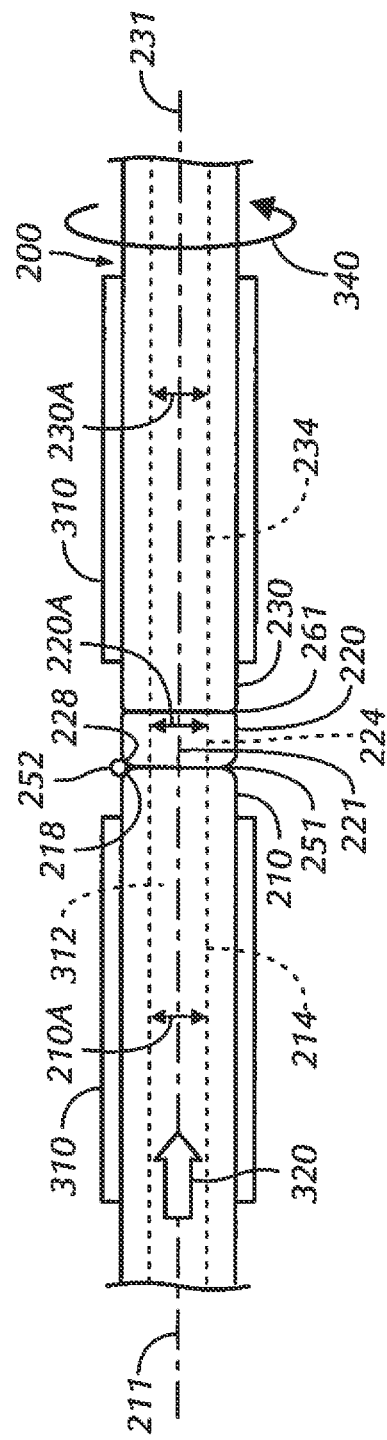
FIG. 6 is a side view of a hypotube joining configuration in accordance with at least one example of the invention.

Referring now to FIGS. 5 and 6, in some examples, the method is described to join the first, second, and third hypotubes 210, 220, 230 to form the apparatus 200, as described above and shown in FIGS. 2A-2C. In some examples, the first hypotube 210 is aligned with the second hypotube 220, such that a first longitudinal axis 211 of the first hypotube 210 substantially coincides with a second longitudinal axis 221 of the second hypotube 220. In further examples, the third hypotube 230 is aligned with the second hypotube 220, such that a third longitudinal axis 231 of the third hypotube 230 substantially coincides with the second longitudinal axis 221 of the second hypotube 220. In some examples, the first, second, and third hypotubes 210, 220, 230 are loaded into one or more alignment members 310. In the examples shown in FIGS. 5 and 6, the one or more alignment members 310 include two containment hypotubes 310, the containment hypotubes 310 being sized such that the first, second, and third hypotubes 210, 220, 230 can fit and freely rotate and slide within the containment hypotubes 310. In this way, the containment tubes 310, in some examples, can be kept stationary and the first, second, and third hypotubes 210, 220, 230 can be rotated, translated, or otherwise moved with respect to the containment tubes 310, if desired, during the joining of the first, second, and third hypotubes 210, 220, 230. Although two containment hypotubes 310 are shown, it is contemplated that a single containment hypotube is used with a cutout, window, or other opening in the containment hypotube to allow access to the abutting first and second hypotubes 210, 220 for joining of the first and second hypotubes 210, 220 and to allow access to the abutting second and third hypotubes 220, 230 for joining of the second and third hypotubes 220, 230. In other examples, other types of alignment devices are contemplated, such as, but not limited to one or more channels within one or more plates, blocks, angle irons, partial tubes, or other members.

In some examples, a force 320 is applied along the first longitudinal axis 211 of the first hypotube 210 to push the first hypotube 210 toward and maintain contact against the second hypotube 220 along a first intersection 251 of the first hypotube 210 and the second hypotube 220, and, in turn, push the second hypotube 220 toward and maintain contact against the third hypotube 230 along a second intersection 261 of the second hypotube 220 and the third hypotube 230. In some examples, the force 320 can be applied to the first hypotube 210 by a pushing device 330 (see FIG. 3). In some examples, the pushing device 330 includes a pushing surface 332 that interfaces with the first hypotube 210. In some examples, the pushing surface 332 abuts a first end of the first hypotube 210. In other examples, the pushing device 330 includes other attachment devices for attaching to the first hypotube 210, including, but not limited to a clamp, a chuck, or the like. The pushing device 330, in some examples, includes a pushing member 334 to generate the force 320 to be applied to the first hypotube 210. In some examples, the pushing member 334 includes a spring to generate the force 320. In other examples, the pushing member 334 includes a piston to generate the force 320. In further examples, the pushing member 334 includes a pneumatic or hydraulic piston to generate the force 320.

In some examples, an alignment wire 312 can be inserted or otherwise placed within the first, second, and third lumens 214, 224, 234 to aid or facilitate in the alignment of the first, second, and third hypotubes 210, 220, 230. In some examples, the alignment wire 312 is sized to be slightly smaller in diameter than the inner diameters 210A, 220A, 230A of the first, second, and third hypotubes 210, 220, 230 in order to fit within and properly align the first, second, and third lumens 214, 224, 234 of the first, second, and third hypotubes 210, 220, 230, but also allow for relatively easy insertion into and withdrawal from the first, second, and third lumens 214, 224, 234. In other examples, no alignment wire 312 is used to align the first, second, and third hypotubes 210, 220, 230, with the containment tubes 310 or other alignment member or members 310 providing for alignment of the first, second, and third hypotubes 210, 220, 230.

In some examples, the first hypotube 210 is joined to the second hypotube 220 at the first intersection 251 of the first hypotube 210 and the second hypotube 220 to form the first joint 250, and the third hypotube 230 is joined to the second hypotube 220 at the second intersection 261 of the third hypotube 230 and the second hypotube 220 to form the second joint 260 (FIGS. 2A-2C). Various techniques can be used to join the first, second, and third hypotubes 210, 220, 230, including, but not limited to, laser welding, ultra-sonic welding, plasma welding, friction welding, soldering, and/or other processes and/or one or more combinations thereof. In some examples, the first, second, and third hypotubes 210, 220, 230 are joined by laser welding the first hypotube 210 to the second hypotube 220 and the second hypotube 220 to the third hypotube 230. In some examples, the laser welding includes the laser emitter or head 360 to deliver one or more laser pulses 362 (see FIG. 3) at the first intersection 251 of the first hypotube 210 and the second hypotube 220 and at the second intersection 261 of the second hypotube 220 and the third hypotube 230. In some examples, the laser emitter or head 360 can include a laser generator, one or more delivery optics, one or more focusing optics, or a combination thereof. In some examples, if the alignment wire 312 is used to facilitate alignment of the first, second, and third hypotubes 210, 220, 230, once at least one laser pulse 362 is delivered at each of the first and second intersections 251, 261, the alignment wire 312 can be removed. The at least one laser pulse 362 at each of the first and second intersections 251, 261 tacks the first and second hypotubes 210, 220 together and the second and third hypotubes 220, 230 together, thereby inhibiting relative movement between the first, second, and third hypotubes 210, 220, 230 so that the alignment wire 312 can be removed from within the first, second, and third hypotubes 210, 220, 230. In some examples, additional laser pulses 362 can be delivered to the first and second intersections 251, 261 to further join the first, second, and third hypotubes 210, 220, 230.

In some examples, relative rotation is imparted between the laser emitter or head 360 and the first, second, and third hypotubes 210, 220, 230 to laser weld around the first and second hypotubes 210, 220 along the first intersection 251 and around the second and third hypotubes 220, 230 along the second intersection 261. In some examples, the first, second, and third hypotubes 210, 220, 230 are rotated with respect to the laser emitter or head 360. For instance, in some examples, the clamping device 350 (see FIG. 3) is attached to the third hypotube 230, the clamping device 350 being rotatable to impart rotation 340 to the third hypotube 230, and, in turn, the first and second hypotubes 210, 220 once the first hypotube 210 is at least tacked to the second hypotube 220 and the second hypotube 220 is at least tacked to the third hypotube 230. In some examples, the first, second, and third hypotubes 210, 220, 230 are rotated to deliver laser pulses 362 along the entire circumference of the first intersection 251 of the first and second hypotubes 210, 220 to create the first joint 250 and along the entire circumference of the second intersection 261 of the second and third hypotubes 220, 230 to create the second joint 260. In other examples, the first, second, and third hypotubes 210, 220, 230 are kept stationary and the laser emitter or head 360 is rotated with respect to the first, second, and third hypotubes 210, 220, 230 in order to laser weld the entire circumference of the first and second intersection 251, 261 to create the first and second joints 250, 260. In some examples, the first joint 250 is formed first between the first and second hypotubes 210, 220. Once the first joint 250 is formed, the first, second, and third hypotubes 210, 220, 230 are translated relative the laser emitter or head 360 (either by moving the first, second, and third hypotubes 210, 220, 230 or by moving the laser emitter or head 360) to align the second intersection 261 with the laser emitter or head 360. Once the laser emitter or head 360 is aligned with the second intersection 261, in some examples, the second joint 260 is formed first between the second and third hypotubes 220, 230. In some examples, each of the first and second intersections 251, 261 are first tacked prior to forming the first and second joints 250, 260. In other examples, the second joint 260 is formed first between the second and third hypotubes 220, 230. Once the second joint 260 is formed, the first, second, and third hypotubes 210, 220, 230 are translated relative the laser emitter or head 360 (either by moving the first, second, and third hypotubes 210, 220, 230 or by moving the laser emitter or head 360) to align the first intersection 251 with the laser emitter or head 360. Once the laser emitter or head 360 is aligned with the first intersection 251, in some examples, the first joint 250 is formed first between the first and second hypotubes 210, 220.

In some examples, one or more pulse profiles of the one or more laser pulses 362 are shaped, tuned, or otherwise configured to deliver energy to the first, second, and third hypotubes 210, 220, 230 at the first and second intersections 251, 261 to sufficiently fuse the first, second, and third hypotubes 210, 220, 230 while at the same time inhibiting, if not preventing, the first, second, and/or third materials of the first, second, and third hypotubes 210, 220, 230 from migrating into the first lumen 214, the second lumen 224, and/or the third lumen 234 to maintain the passageway 204 of the apparatus 200 (FIGS. 2A-2C) free from obstructions. In some examples, the one or more laser pulses 362 are tuned or configured to deliver energy to the first, second, and third hypotubes 210, 220, 230 at the first and second intersections 251, 261 to sufficiently fuse the first, second, and third hypotubes 210, 220, 230 while at the same time inhibiting, if not preventing, the first, second, and/or third materials of the first, second, and third hypotubes 210, 220, 230 from extending outwardly from the first sidewall 212, the second sidewall 222, and/or the third sidewall 232 to maintain the sidewall 202 of the apparatus 200 (FIGS. 2A-2C) free from obstructions.

In some examples, the first and second intersections 251, 261 are disposed between the containment hypotubes 310 to allow access by the laser emitter or head 360 and the one or more laser pulses 362 to the first and second intersections 251, 261 in order to form the first and second joints 250, 260. In other examples in which other alignment devices are contemplated, such as a single containment hypotube with a cutout, window, or other opening; one or more channels within one or more plates, blocks, angle irons, partial tubes, or other members; to name a few, the first and second intersections 251, 261 are located to allow access to the first and second intersections 251, 261 by the laser emitter or head 360 and the one or more laser pulses 362.

In some examples, as shown in FIG. 5, the first joint 250 is formed from the first material of the first hypotube 210 and the second material of the second hypotube 220 without the use of a filler. In other examples, as shown in FIG. 6, a filler 252 is used to make the first joint 250, such that the first joint 250 is formed from the first material of the first hypotube 210, the second material of the second hypotube 220, and the filler 252. In this way, in some examples, the filler 252 is added at the first intersection 251 of the first and second hypotubes 210, 220 prior to joining the first and second hypotubes 210, 220. Once the filler 252 is present at the intersection, the one or more laser pulses 362 can be applied to the first intersection 251 in order to fuse the first material, the second material, and the filler 252, such that the first joint 250 includes a combination of the first material, the second material, and the filler 252. The filler 252, in various examples, can include one or more of MP35N, cobalt (Co), nickel (Ni), and/or copper (Cu). The filler 252, in various examples, can be introduced to the first intersection 251 in various ways, such as, but not limited to, adding the filler 252 in the form of a wire, a powder, or a ball. In some examples, the filler 252 is introduced with the rotation 340 of the first and second hypotubes 210, 220. In other examples, if the first and second hypotubes 210, 220 are kept stationary, the filler 252 can be rotated around the first and second hypotubes 210, 220 along with the laser emitter or head 360 in order to introduce the filler 252 prior to laser welding. In some examples, the first intersection 251 is disposed between the containment hypotubes 310 to allow access to the first intersection 251 to add the filler 252 prior to laser welding. In other examples in which other alignment devices are contemplated, such as a single containment hypotube with a cutout, window, or other opening; one or more channels within one or more plates, blocks, angle irons, partial tubes, or other members; to name a few, the first intersection 251 is located to allow access to the first intersection 251 in order to add the filler 252 to the first intersection 251 prior to laser welding.

In some examples, at least one of the first and second hypotubes 210, 220 can include a reduced edge 218, 228 along the first intersection 251. For instance, in some examples, the first hypotube 210 includes a first reduced edge 218, and the second hypotube 220 includes a second reduced edge 228. In various examples, the first and second hypotubes 210, 220 can be ground down, cut, filed, or otherwise removed to form the first and second reduced edges 218, 228. In other examples, the first and second hypotubes 210, 220 can be formed to include the first and second reduced edges 218, 228. The first and second reduced edges 218, 220, in some examples, can include a rounded shape, a tapered shape, or the like. With one or both of the first and second hypotubes 210, 220 including the reduced edge 218, 228, the filler 252 can be added to the first intersection 251 and the first intersection 251 can be welded to form the first joint 250 without the first joint 250 expanding beyond the first and second inner diameters 210A, 220A of the first and second hypotubes 210, 220 or the first and second outer diameters 210B, 220B of the first and second hypotubes 210, 220, thereby maintaining substantially consistent dimensions of the passageway 204 and the sidewall 202 of the apparatus 200. That is, with one or both of the first and second reduced edges 218, 228, the removal of the first and/or second materials of the first and/or second hypotubes 210, 220 makes room for the addition of the filler 252 without increasing the overall volume of the materials making up the first joint 250 to allow for the dimensions of the first joint 250 to remain substantially consistent with the dimensions of the first hypotube 210 and the second hypotube 220, thereby allowing for the passageway 204 and the sidewall 202 of the apparatus 200 to maintain substantially consistent dimensions along the length of the apparatus 200. In some examples, both of the first and second hypotubes 210, 220 include reduced edges 218, 228. In other examples, only the first hypotube 210 includes the first reduced edge 218, with the second hypotube 220 including a normal, unreduced edge. In still other examples, only the second hypotube 220 includes the second reduced edge 228, with the first hypotube 210 including a normal, unreduced edge.

In some examples, once the first and second joints 250, 260 are completed, the first, second, and third hypotubes 210, 220, 230 are joined together to form the apparatus 200, which can be removed from within the containment tubes 310 or other alignment device(s). The apparatus 200, in some examples, forms a continuous hypotube with differing characteristics along the length of the apparatus 200 due to the different materials used for the first, second, and third hypotubes 210, 220, 230, which make up the apparatus 200. For instance, in the example in which the first hypotube 210 is formed from Nitinol, the second hypotube 220 is formed from MP35N, and the third hypotube 230 is formed from stainless steel, the apparatus 200 includes flexibility, shape retention, and kink-resistance in the portion of the apparatus 200 formed by the first hypotube 210 and stiffness and torquability in the portion of the apparatus 200 formed by the second and third hypotubes 220, 230.

Although the configurations for joining the hypotubes 110, 120, 210, 220, 230 shown in FIGS. 3-6 and described herein include the pushing device 330 interacting with the first hypotube 110, 210 and the clamping device 350 interacting with the second hypotube 120 (FIGS. 3 and 4) and the third hypotube 230 (FIGS. 5 and 6), such configurations were used as merely exemplary and should not be considered limiting. As such, other configurations are contemplated herein. For instance, in some examples, the pushing device 330 can interact with the second hypotube 120 or the third hypotube 230, and the clamping device 350 can interact with the first hypotube 110, 210. In other examples, pushing devices 330 can be used on both sides, such that one pushing device 330 interacts with the first hypotube 110, 210 and another pushing device 330 interacts with the second hypotube 120 or the third hypotube 230, so that the pushing devices 330 can push the hypotubes 110, 120, 210, 220, 230 together from both sides. In still other examples, regardless of whether the pushing device 330 is located on the left side, the right side, or both sides, clamping devices 350 can be used on both sides, such that one clamping device 350 interacts with the first hypotube 110, 210 and another clamping device 350 interacts with the second hypotube 120 or the third hypotube 230, so that the clamping devices 350 can rotate the hypotubes 110, 120, 210, 220, 230 from both sides. In still other examples, the pushing device 330 and the clamping device 350 can be combined into a single pushing/clamping device that can apply a force on the hypotubes 110, 120, 210, 220, 230 and can also impart a rotation on the hypotubes 110, 120, 210, 220, 230. Such a combined pushing/clamping device can be located on either side (to interact with either (1) the first hypotubes 110, 210 or (2) the second hypotube 120 or the third hypotube 230) or on both sides (to interact with both (1) the first hypotubes 110, 210 and (2) the second hypotube 120 or the third hypotube 230).

Figure 7:
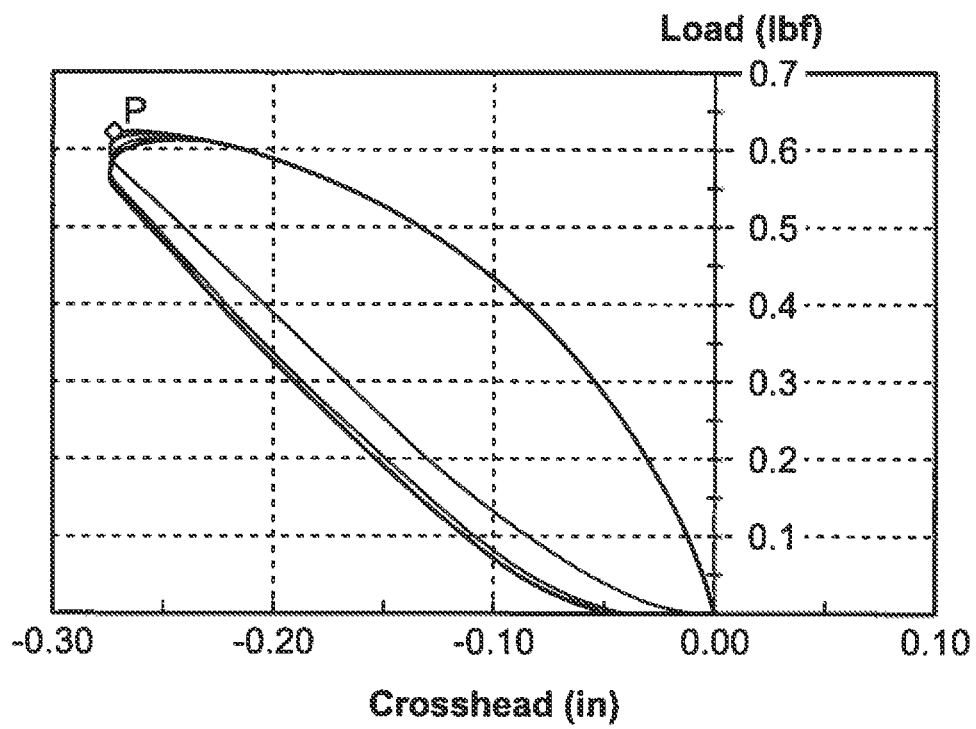
FIG. 7 is a graph showing bend test performance of hypotubes joined in accordance with at least one example of the invention.

Referring to FIG. 7, results of an ISO 9626 Annex D test are shown. (See ISO 9626.) This test determines the resistance of tube breakage during dynamic bend testing. Although the test is designed for homogenous stainless steel hypotubes and not for welded joint assemblies of different materials, this test was applied to various sample apparatuses 100, 200 including the joints 150, 250, 260 described herein to help measure the integrity of the joints 150, 250, 260. The maximum load condition was selected to provide the highest stress to the weld joint, the conditions being: 17.5 mm distance between the rigid support and point of bending force; the stainless steel or MP35N hypotube loaded in the rigid support; and the weld joint at a location of 12 mm from the rigid support point. All other test conditions of ISO 9626 Annex D were implemented for thin-walled tubing. (See ISO 9626.) The graph displays the force over distance for the set number of cycles, as defined in ISO 9626 Annex D. The graph does not display a breakage occurrence during the test, indicating the sample met the requirements for ISO 9626 Annex D.

Figure 8:
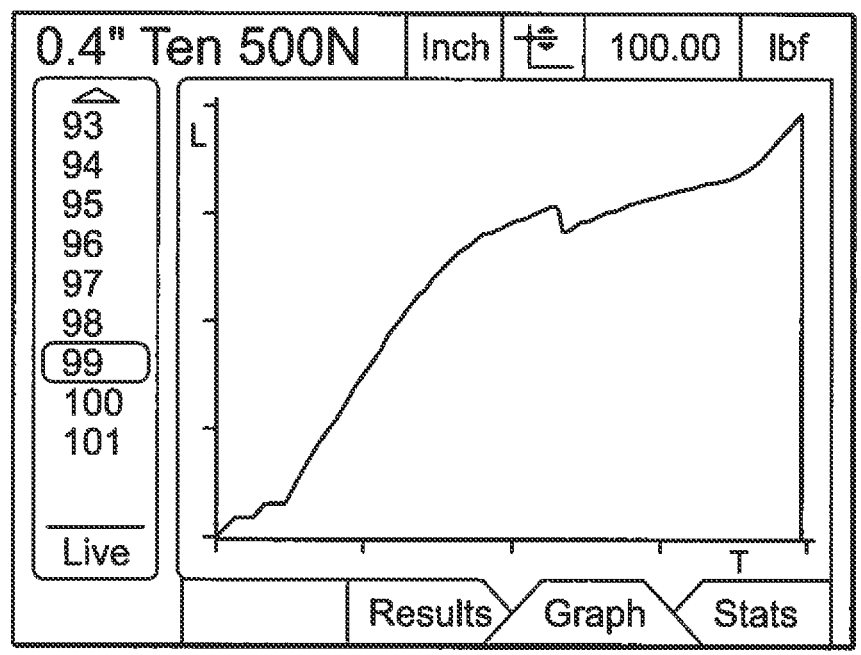
FIG. 8 is a graph showing performance of hypotubes joined in accordance with at least one example of the invention.

Referring to FIG. 8, a stress-strain characteristics curve of a Nitinol-to-MP35N weld joint, such as the first joint 150, 250 of samples of the apparatuses 100, 200, is shown. The weld joint 150, 250 exceeded the loading plateau stress of a Nitinol hypotube, thereby demonstrating a ductile robust weld joint. The Ultimate Tensile Strength (UTS) for all tested samples are displayed in FIGS. 9 and 10.

Figure 9:
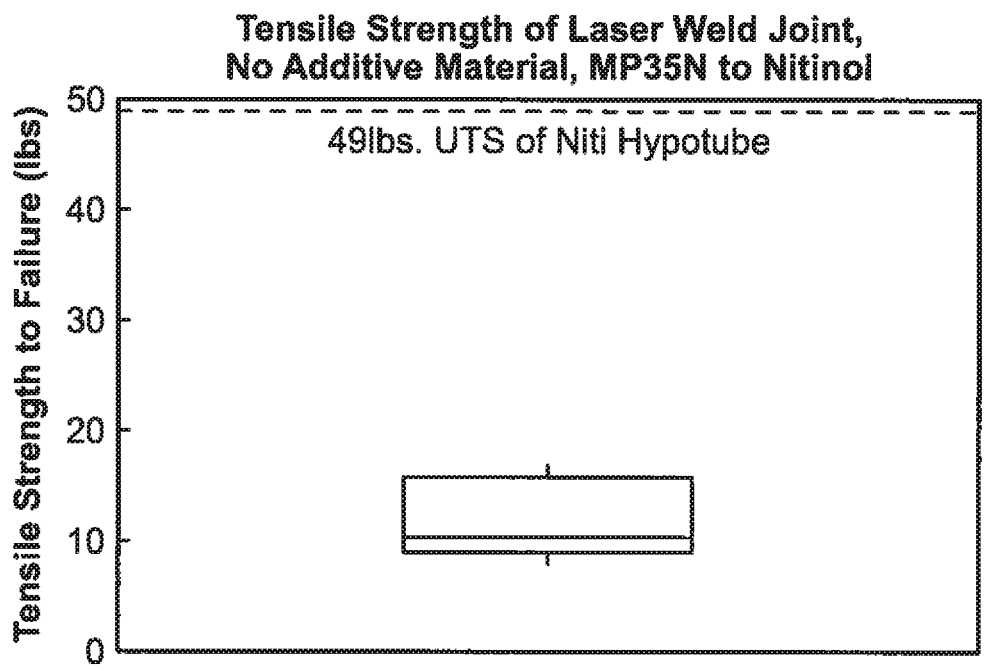
FIG. 9 is a graph showing tensile strength of hypotubes joined in accordance with at least one example of the invention.

Referring to FIG. 9, results of an UTS test are shown for weld joints 150, 250 of sample apparatuses 100, 200 without additive or filler material 152, 252 included in the joints 150, 250.

Figure 10:
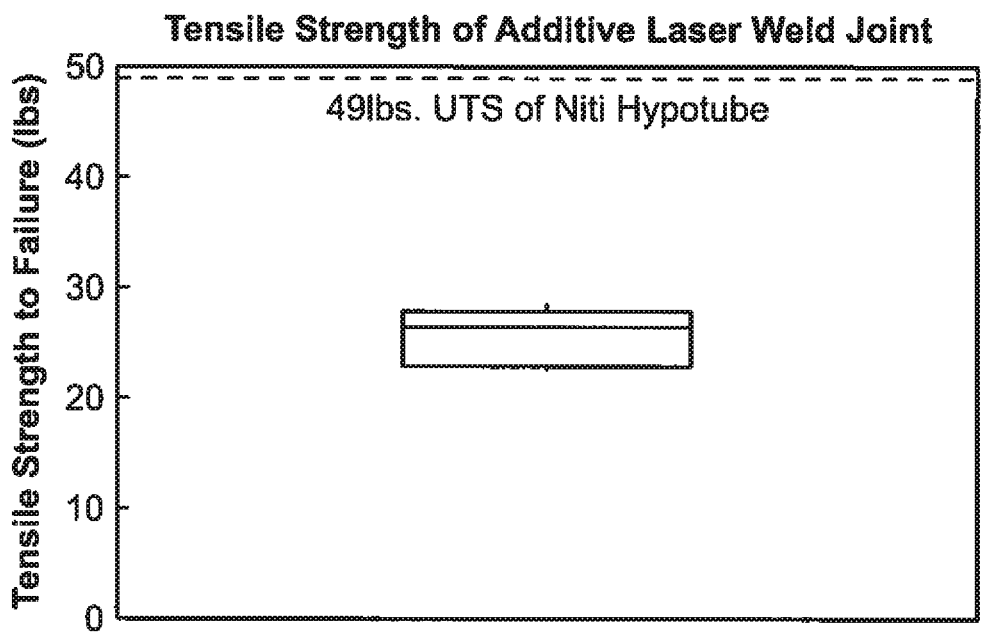
FIG. 10 is a graph showing tensile strength of hypotubes joined in accordance with at least one example of the invention.

Referring to FIG. 10, results of a UTS test are shown for weld joints 150, 250 with additive or filler material 152, 252 included in the joints 150, 250.

The present inventors have recognized various advantages of the subject matter described herein. The present inventors have recognized, among other things, that the present subject matter can be used to join hypotubes to be used within a medical device in order to provide the medical device with a passageway therein while at the same time giving the medical device differing properties along its length. Joining hypotubes can be difficult due to the small size of the hypotubes. Moreover, maintaining a consistent passageway within the joined hypotubes can also be difficult due to the potential of material from the at least one joint entering the passageway during the joining process. The present inventors have recognized that the present subject matter can be used to join hypotubes of different materials to maintain a consistent passageway therein and provide the joined hypotubes with differing properties along the length of the joined hypotubes due to the different materials. The present inventors have further recognized that joined hypotubes of the present subject matter can be used within a medical device, such as, for instance, a guidewire. While various advantages of the example apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A method of joining two or more hypotubes together to form an apparatus, the method comprising:

aligning a first hypotube with a second hypotube, wherein a first longitudinal axis of the first hypotube coincides with a second longitudinal axis of the second hypotube, wherein:
  the first hypotube is formed from a first material and includes a first sidewall and a first lumen defined within the first sidewall and extending through the first hypotube, the first hypotube including a first inner diameter and a first outer diameter; and
  the second hypotube is formed from a second material different from the first material and includes a second sidewall and a second lumen defined within the second sidewall and extending through the second hypotube, the second hypotube including a second inner diameter and a second outer diameter, wherein the second inner diameter is similar to the first inner diameter and the second outer diameter is similar to the first outer diameter, wherein aligning the first hypotube with the second hypotube includes inserting an alignment wire within the first lumen and the second lumen to facilitate alignment of the first and second hypotubes;
applying a force along the first longitudinal axis of the first hypotube to push the first hypotube toward and maintain contact against the second hypotube along a first intersection of the first hypotube and the second hypotube;
after aligning the first hypotube with the second hypotube, laser welding the first hypotube to the second hypotube at the first intersection of the first hypotube and the second hypotube to form a first joint, the first joint including a combination of the first material and the second material, the first joint including a first joint inner diameter that is similar to the first and second inner diameters, wherein the apparatus includes a sidewall and a passageway defined within the sidewall and extending through the apparatus, the sidewall formed by the first sidewall, the second sidewall, and the first joint, the passageway formed by the first lumen, the second lumen, and the first joint inner diameter, the apparatus including an outer diameter that is substantially consistent along a length of the apparatus and an inner diameter that is substantially consistent along a length of the apparatus;
aligning a third hypotube with the second hypotube, wherein a third longitudinal axis of the third hypotube coincides with the second longitudinal axis of the second hypotube, wherein the third hypotube is formed from a third material different from the second material and including a third sidewall and a third lumen defined within the third sidewall and extending through the third hypotube, the third hypotube including a third inner diameter and a third outer diameter, wherein the third inner diameter is similar to the second inner diameter and the third outer diameter is similar to the second outer diameter;
applying a force along the second longitudinal axis of the second hypotube to push the second hypotube toward and maintain contact against the third hypotube along a second intersection of the second hypotube and the third hypotube; and
after aligning the third hypotube with the second hypotube, laser welding the third hypotube to the second hypotube at the second intersection of the second hypotube and the third hypotube to form a second joint, the second joint including a combination of the second material and the third material, the second joint including a second joint inner diameter that is similar to the second and third inner diameters, wherein the sidewall of the apparatus is formed by the first sidewall, the second sidewall, the third sidewall, the first joint, and the second joint, and the passageway is formed by the first lumen, the second lumen, the third lumen, the first joint inner diameter, and the second joint inner diameter.

2. The method of claim 1, wherein the laser welding including delivering one or more laser pulses at the first intersection of the first hypotube and the second hypotube.

3. The method of claim 2, wherein the laser welding includes imparting relative rotation between a laser emitter and the first and second hypotubes to laser weld around the first and second hypotubes along the first intersection.

4. The method of claim 1, comprising adding a filler at the first intersection of the first and second hypotubes prior to the laser welding of the first and second hypotubes, wherein the first joint includes a combination of the first material, the second material, and the filler.

5. The method of claim 1, wherein the first material includes Nitinol.

6. The method of claim 1, wherein the second material includes a nickel-cobalt-based alloy material.

7. The method of claim 1, wherein the laser welding of the first hypotube to the second hypotube includes the first joint including a first joint outer diameter that is similar to the first and second outer diameters.

8. The method of claim 1, wherein the laser welding including delivering one or more laser pulses at the second intersection of the third hypotube and the second hypotube.

9. The method of claim 1, wherein the laser welding includes imparting relative rotation between a laser emitter and the second and third hypotubes to laser weld around the second and third hypotubes along the second intersection.

10. The method of claim 1, wherein aligning the third hypotube with the second hypotube includes inserting an alignment wire within the second lumen and the third lumen to facilitate alignment of the second and third hypotubes.

11. The method of claim 1, wherein the third material includes stainless steel.

12. The method of claim 1, wherein the laser welding of the third hypotube to the second hypotube includes the second joint including a second joint outer diameter that is similar to the second and third outer diameters.

13. A method of joining three hypotubes together to form an apparatus, the method comprising:
  aligning a first hypotube with a second hypotube, wherein a first longitudinal axis of the first hypotube coincides with a second longitudinal axis of the second hypotube, wherein:
    the first hypotube is formed from a first material and includes a first sidewall and a first lumen defined within the first sidewall and extending through the first hypotube, the first hypotube including a first inner diameter and a first outer diameter; and
    the second hypotube is formed from a second material different from the first material and includes a second sidewall and a second lumen defined within the second sidewall and extending through the second hypotube, the second hypotube including a second inner diameter and a second outer diameter, wherein the second inner diameter is similar to the first inner diameter and the second outer diameter is similar to the first outer diameter, wherein aligning the first hypotube with the second hypotube includes inserting a first alignment wire within the first lumen and the second lumen to facilitate alignment of the first and second hypotubes;

applying a force along the first longitudinal axis of the first hypotube to push the first hypotube toward and maintain contact against the second hypotube along a first intersection of the first hypotube and the second hypotube;

after aligning the first hypotube with the second hypotube, laser welding the first hypotube to the second hypotube at the first intersection of the first hypotube and the second hypotube to form a first joint, the first joint including a combination of the first material and the second material, the first joint including a first joint inner diameter that is similar to the first and second inner diameters, wherein the apparatus includes a sidewall and a passageway defined within the sidewall and extending through the apparatus, the sidewall formed by the first sidewall, the second sidewall, and the first joint, the passageway formed by the first lumen, the second lumen, and the first joint inner diameter, the apparatus including an outer diameter that is substantially consistent along a length of the apparatus and an inner diameter that is substantially consistent along a length of the apparatus, the laser welding including delivering one or more laser pulses at the first intersection of the first hypotube and the second hypotube;

aligning a third hypotube with the second hypotube, wherein a third longitudinal axis of the third hypotube coincides with the second longitudinal axis of the second hypotube, wherein the third hypotube is formed from a third material different from the second material and including a third sidewall and a third lumen defined within the third sidewall and extending through the third hypotube, the third hypotube including a third inner diameter and a third outer diameter, wherein the third inner diameter is similar to the second inner diameter and the third outer diameter is similar to the second outer diameter, wherein aligning the third hypotube with the second hypotube includes inserting a second alignment wire within the second lumen and the third lumen to facilitate alignment of the second and third hypotubes;

applying a force along the second longitudinal axis of the second hypotube to push the second hypotube toward and maintain contact against the third hypotube along a second intersection of the second hypotube and the third hypotube; and after aligning the third hypotube with the second hypotube, laser welding the third hypotube to the second hypotube at the second intersection of the second hypotube and the third hypotube to form a second joint, the second joint including a combination of the second material and the third material, the second joint including a second joint inner diameter that is similar to the second and third inner diameters, wherein the sidewall of the apparatus is formed by the first sidewall, the second sidewall, the third sidewall, the first joint, and the second joint, and the passageway is formed by the first lumen, the second lumen, the third lumen, the first joint inner diameter, and the second joint inner diameter, the laser welding including delivering one or more laser pulses at the second intersection of the third hypotube and the second hypotube.

14. The method of claim 13, wherein the laser welding includes imparting relative rotation between a laser emitter and:

the first and second hypotubes to laser weld around the first and second hypotubes along the first intersection; and the second and third hypotubes to laser weld around the second and third hypotubes along the second intersection.

15. The method of claim 13, comprising adding a filler at the first intersection of the first and second hypotubes prior to laser welding the first and second hypotubes, wherein the first joint includes a combination of the first material, the second material, and the filler.

16. The method of claim 13, comprising adding a filler at the second intersection of the second and third hypotubes prior to laser welding the second and third hypotubes, wherein the second joint includes a combination of the second material, the third material, and the filler.

17. The method of claim 13, wherein laser welding the first hypotube to the second hypotube includes the first joint including a first joint outer diameter that is similar to the first and second outer diameters.

18. The method of claim 13, wherein laser welding the third hypotube to the second hypotube includes the second joint including a second joint outer diameter that is similar to the second and third outer diameters.

19. The method of claim 13, wherein the first material includes Nitinol.

20. The method of claim 13, wherein the second material includes a nickel-cobalt-based alloy material.

21. The method of claim 13, wherein the third material includes stainless steel.

22. A method of joining multiple hypotubes together to form an apparatus, the method comprising:

aligning:
  a first hypotube with a second hypotube, wherein a first longitudinal axis of the first hypotube coincides with a second longitudinal axis of the second hypotube, wherein:
    the first hypotube is formed from a first material and includes a first sidewall and a first lumen defined within the first sidewall and extending through the first hypotube, the first hypotube including a first inner diameter and a first outer diameter; and
    the second hypotube is formed from a second material different from the first material and includes a second sidewall and a second lumen defined within the second sidewall and extending through the second hypotube, the second hypotube including a second inner diameter and a second outer diameter, wherein the second inner diameter is similar to the first inner diameter and the second outer diameter is similar to the first outer diameter, the aligning including inserting a first alignment wire within the first lumen and the second lumen to facilitate alignment of the first and second hypotubes; and
  a third hypotube with the second hypotube, wherein a third longitudinal axis of the third hypotube coincides with the second longitudinal axis of the second hypotube, wherein the third hypotube is formed from a third material different from the second material and including a third sidewall and a third lumen defined within the third sidewall and extending through the third hypotube, the third hypotube including a third inner diameter and a third outer diameter, wherein the third inner diameter is similar to the second inner diameter and the third outer diameter is similar to the second outer diameter, the aligning including inserting a second alignment wire within the second lumen and the third lumen to facilitate alignment of the second and third hypotubes;

applying a force along:
   the first longitudinal axis of the first hypotube to push the first hypotube toward and maintain contact against the second hypotube along a first intersection of the first hypotube and the second hypotube; and
   the second longitudinal axis of the second hypotube to push the second hypotube toward and maintain contact against the third hypotube along a second intersection of the second hypotube and the third hypotube; and after aligning the first and third hypotubes with the second hypotube, laser welding:
   the first hypotube to the second hypotube at the first intersection of the first hypotube and the second hypotube to form a first joint, the first joint including a combination of the first material and the second material, the first joint including a first joint inner diameter that is similar to the first and second inner diameters, wherein the apparatus includes a sidewall and a passageway defined within the sidewall and extending through the apparatus, the sidewall formed by the first sidewall, the second sidewall, and the first joint, the passageway formed by the first lumen, the second lumen, and the first joint inner diameter, the apparatus including an outer diameter that is substantially consistent along a length of the apparatus and an inner diameter that is substantially consistent along a length of the apparatus, the laser welding including delivering one or more laser pulses at the first intersection of the first hypotube and the second hypotube; and
   the third hypotube to the second hypotube at the second intersection of the second hypotube and the third hypotube to form a second joint, the second joint including a combination of the second material and the third material, the second joint including a second joint inner diameter that is similar to the second and third inner diameters, wherein the sidewall of the apparatus is formed by the first sidewall, the second sidewall, the third sidewall, the first joint, and the second joint, and the passageway is formed by the first lumen, the second lumen, the third lumen, the first joint inner diameter, and the second joint inner diameter, the laser welding including delivering one or more laser pulses at the second intersection of the third hypotube and the second hypotube, wherein the laser welding includes imparting relative rotation between a laser emitter and:
      the first and second hypotubes to laser weld around the first and second hypotubes along the first intersection; and
      the second and third hypotubes to laser weld around the second and third hypotubes along the second intersection.

23. The method of claim 22, comprising adding a filler at:
   the first intersection of the first and second hypotubes prior to laser welding the first and second hypotubes, wherein the first joint includes a combination of the first material, the second material, and the filler; and
   at the second intersection of the second and third hypotubes prior to laser welding the second and third hypotubes, wherein the second joint includes a combination of the second material, the third material, and the filler, wherein the filler is selected from the group of a nickel-cobalt-based alloy material, cobalt, nickel, and copper.

24. The method of claim 1, comprising removing the alignment wire from within the first lumen and the second lumen after joining the first hypotube to the second hypotube.

25. The method of claim 13, comprising:
   removing the first alignment wire from within the first lumen and the second lumen after joining the first hypotube to the second hypotube; and
   removing the second alignment wire from within the second lumen and the third lumen after joining the second hypotube to the third hypotube.

26. The method of claim 22, comprising:
   removing the first alignment wire from within the first lumen and the second lumen after joining the first hypotube to the second hypotube; and
   removing the second alignment wire from within the second lumen and the third lumen after joining the second hypotube to the third hypotube.

* * * * *